US010736924B2

(12) United States Patent
Cani et al.

(10) Patent No.: US 10,736,924 B2
(45) Date of Patent: Aug. 11, 2020

(54) **USE OF PASTEURIZED *AKKERMANSIA* FOR TREATING METABOLIC DISORDERS**

(71) Applicants: Université Catholique de Louvain, Louvain la Neuve (BE); WAGENINGEN UNIVERSITEIT, Wageningen (NL)

(72) Inventors: Patrice Cani, Brussels (BE); Amandine Everard, Wavre (BE); Hubert Plovier, Rumes (BE); Céline Druart, Quaregon (BE); Willem De Vos, Ede (NL); Clara Belzer, Wageningen (NL)

(73) Assignees: UNIVERSITÉ CATHOLIQUE DE LOUVAIN, Louvain-la-Neuve (BE); WAGENINGEN UNIVERSITEIT, Wageningen (NL)

( * ) Notice: Subject to any disclaimer, the term of this patent is extended or adjusted under 35 U.S.C. 154(b) by 46 days.

(21) Appl. No.: 15/759,381

(22) PCT Filed: Sep. 9, 2016

(86) PCT No.: PCT/EP2016/071327
§ 371 (c)(1),
(2) Date: Mar. 12, 2018

(87) PCT Pub. No.: WO2017/042347
PCT Pub. Date: Mar. 16, 2017

(65) Prior Publication Data
US 2018/0250347 A1    Sep. 6, 2018

(30) Foreign Application Priority Data

Sep. 10, 2015   (EP) .................................. 15184758

(51) Int. Cl.
| | | |
|---|---|---|
| *A61K 35/741* | (2015.01) | |
| *A61K 9/00* | (2006.01) | |
| *A23L 33/105* | (2016.01) | |
| *A61Q 19/06* | (2006.01) | |
| *A61K 8/99* | (2017.01) | |
| *A23L 33/135* | (2016.01) | |
| *A61P 3/04* | (2006.01) | |

(52) U.S. Cl.
CPC .......... *A61K 35/741* (2013.01); *A23L 33/105* (2016.08); *A23L 33/135* (2016.08); *A61K 8/99* (2013.01); *A61K 9/0053* (2013.01); *A61P 3/04* (2018.01); *A61Q 19/06* (2013.01); *A23V 2002/00* (2013.01); *A61K 2800/92* (2013.01)

(58) Field of Classification Search
CPC .................................................... A23L 33/135
See application file for complete search history.

(56) References Cited

U.S. PATENT DOCUMENTS

| | | |
|---|---|---|
| 10,149,870 B2 | 12/2018 | Kaplan et al. |
| 2012/0083514 A1 | 4/2012 | Prevost et al. |
| 2012/0183514 A1 | 7/2012 | Mercenier et al. |
| 2013/0224155 A1 | 8/2013 | Kaplan et al. |

FOREIGN PATENT DOCUMENTS

| | | | |
|---|---|---|---|
| EP | 2 030 623 | 3/2009 | |
| WO | WO 2008076696 | 6/2008 | |
| WO | WO2014/075745 | * 5/2014 | ........... A61K 35/741 |
| WO | WO 2014/076246 | 5/2014 | |

OTHER PUBLICATIONS

International Search Report, PCT/EP2016/071327, dated Dec. 6, 2016.
Berer et al., "Commensal microbiota and myelin autoantigen cooperate to trigger autoimmune demyelination", Nature. Oct. 26, 2011;479(7374):538-41.
De Weerth et al., "Crying in infants: on the possible role of intestinal microbiota in the development of colic", Gut Microbes. Sep.-Oct. 2013;4(5):416-21.
De Weerth et al., "Intestinal microbiota of infants with colic: development and specific signatures", Pediatrics. Feb. 2013;131(2):e550-8.
Delzenne et al., "Interaction between obesity and the gut microbiota: relevance in nutrition", Annu Rev Nutr. Aug. 21, 2011;31:15-31.
Derrien et al., "*Akkermansia muciniphila* gen. nov., sp. nov., a human intestinal mucin-degrading bacterium", Int J Syst Evol Microbiol. Sep. 2004;54(Pt 5):1469-76.
Derrien et al., "The Mucin degrader Akkermansia muciniphila is an abundant resident of the human intestinal tract", Appl Environ Microbiol. Mar. 2008;74(5):1646-8.
Derrien et al., "Modulation of mucosal immune response, tolerance, and proliferation in mice colonized by the mucin-degrader Akkermansia muciniphila", Front Microbiol. Aug. 1, 2011;2:166.
Everard et al., "Responses of gut microbiota and glucose and lipid metabolism to prebiotics in genetic obese and diet-induced leptin-resistant mice", Diabetes, 2011, 60(11):2775-86.
Everard et al., "Cross-talk between Akkermansia muciniphila and intestinal epithelium controls diet-induced obesity", Proc Natl Acad Sci U S A. May 28, 2013;110(22):9066-71.
Goris et al., "DNA-DNA hybridization values and their relationship to whole-genome sequence similarities", Int J Syst Evol Microbiol. Jan. 2007;57(Pt 1):81-91.

(Continued)

*Primary Examiner* — Bin Shen
(74) *Attorney, Agent, or Firm* — Lathrop GPM LLP; James H. Velema, Esq.

(57) ABSTRACT

The present invention relates to pasteurized *Akkermansia muciniphila* or fragments thereof for treating a metabolic disorder in a subject in need thereof. The present invention also relates to a composition, a pharmaceutical composition and a medicament comprising pasteurized *Akkermansia muciniphila* or fragments thereof for treating a metabolic disorder. The present invention also relates to the use of pasteurized *Akkermansia muciniphila* or fragments thereof for promoting weight loss in a subject in need thereof.

14 Claims, 14 Drawing Sheets

Specification includes a Sequence Listing.

(56) References Cited

OTHER PUBLICATIONS

Harach et al., "Reduction of Alzheimer's disease beta-amyloid pathology in the absence of gut microbiota", arXiv:1509.02273.

Hsiao et al., "Microbiota modulate behavioral and physiological abnormalities associated with neurodevelopmental disorders", Cell. Dec. 19, 2013;155(7):1451-63.

Louis et al., "The gut microbiota, bacterial metabolites and colorectal cancer", Nat Rev Microbiol. Oct. 2014;12(10):661-72.

Nylund et al., "Severity of atopic disease inversely correlates with intestinal microbiota diversity and butyrate-producing bacteria", Allergy. Feb. 2015;70(2):241-4.

Rajilic-Stojanovic et al., "The first 1000 cultured species of the human gastrointestinal microbiota", FEMS Microbiol Rev. 2014, 38(5): 996-1047.

Rajilic-Stojanovic et al.,"Phylogenetic analysis of dysbiosis in ulcerative colitis during remission", Inflamm Bowel Dis. Mar. 2013;19(3):481-8.

Reunanen et al., "Akkermansia muciniphila Adheres to Enterocytes and Strengthens the Integrity of the Epithelial Cell Layer", Appl Environ Microbiol. Jun. 2015;81(11):3655-62.

Scheperjans et al., "Gut microbiota are related to Parkinson's disease and clinical phenotype", Mov Disord. Mar. 2015;30(3):350-8.

Van Passel et al., "The genome of Akkermansia muciniphila, a dedicated intestinal mucin degrader, and its use in exploring intestinal metagenomes", PLoS One. Mar. 3, 2011;6(3):e16876.

Wolodarska et al., "An integrative view of microbiome-host interactions in inflammatory bowel diseases", Cell Host Microbe. May 13, 2015;17(5):577-91.

Zitvogel et al., "Cancer and the gut microbiota: an unexpected link", Sci Transl Med. Jan. 21, 2015;7(271):271ps1.

Zoetendal et al., "High-throughput diversity and functionality analysis of the gastrointestinal tract microbiota", Gut 2008, 57: 1605-1615.

* cited by examiner

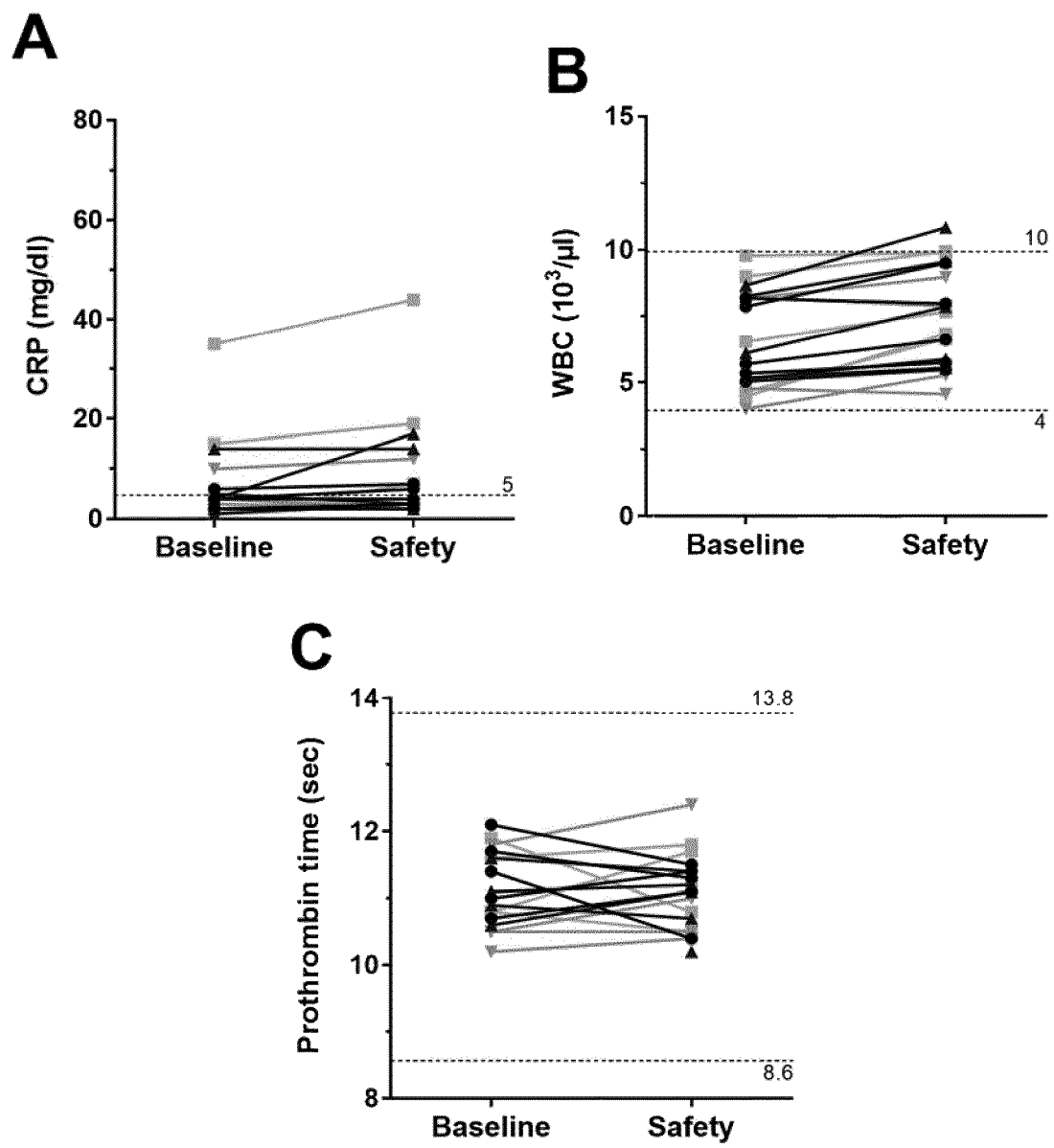
FIG. 14A-C

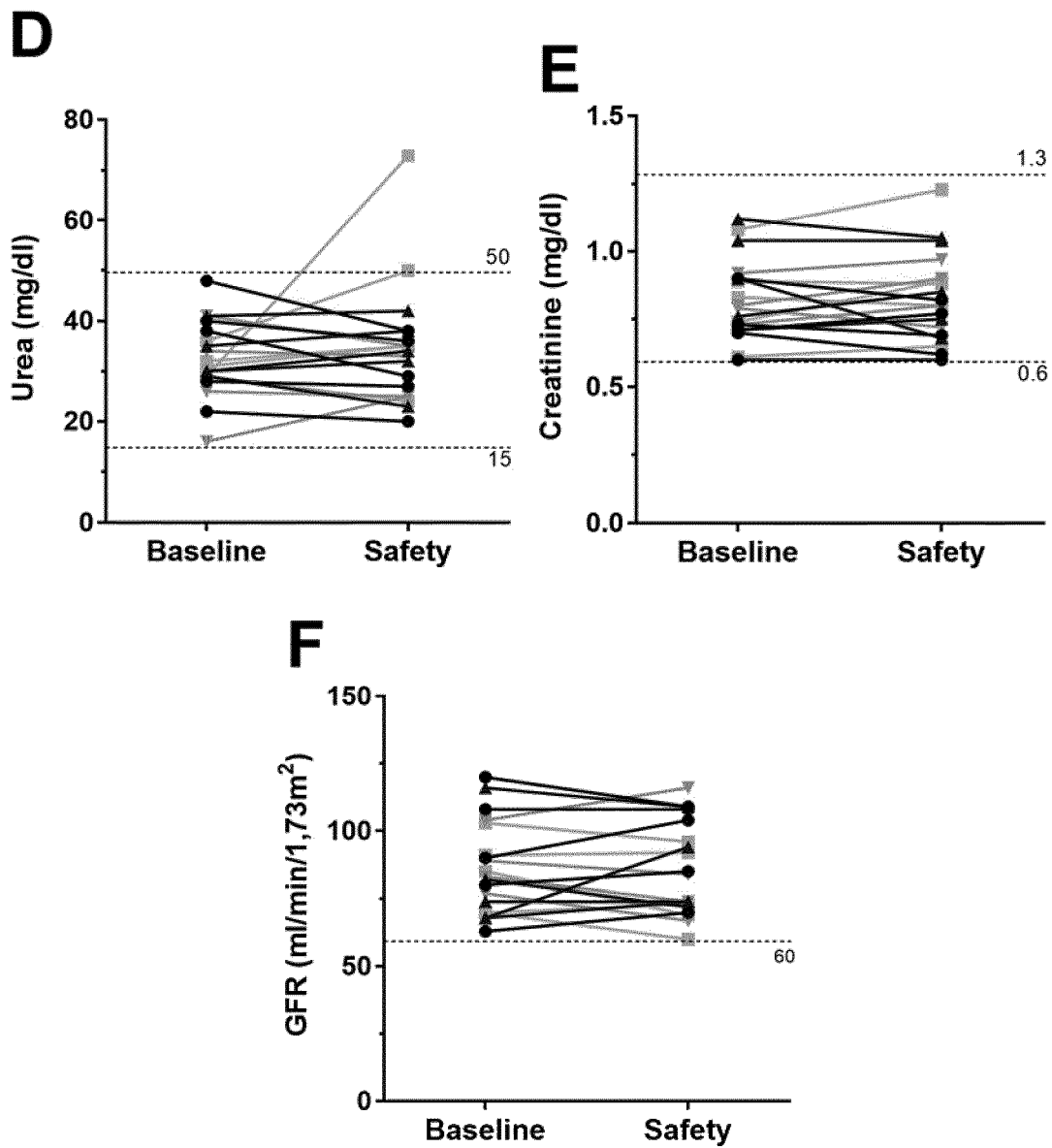
FIG. 14D-F

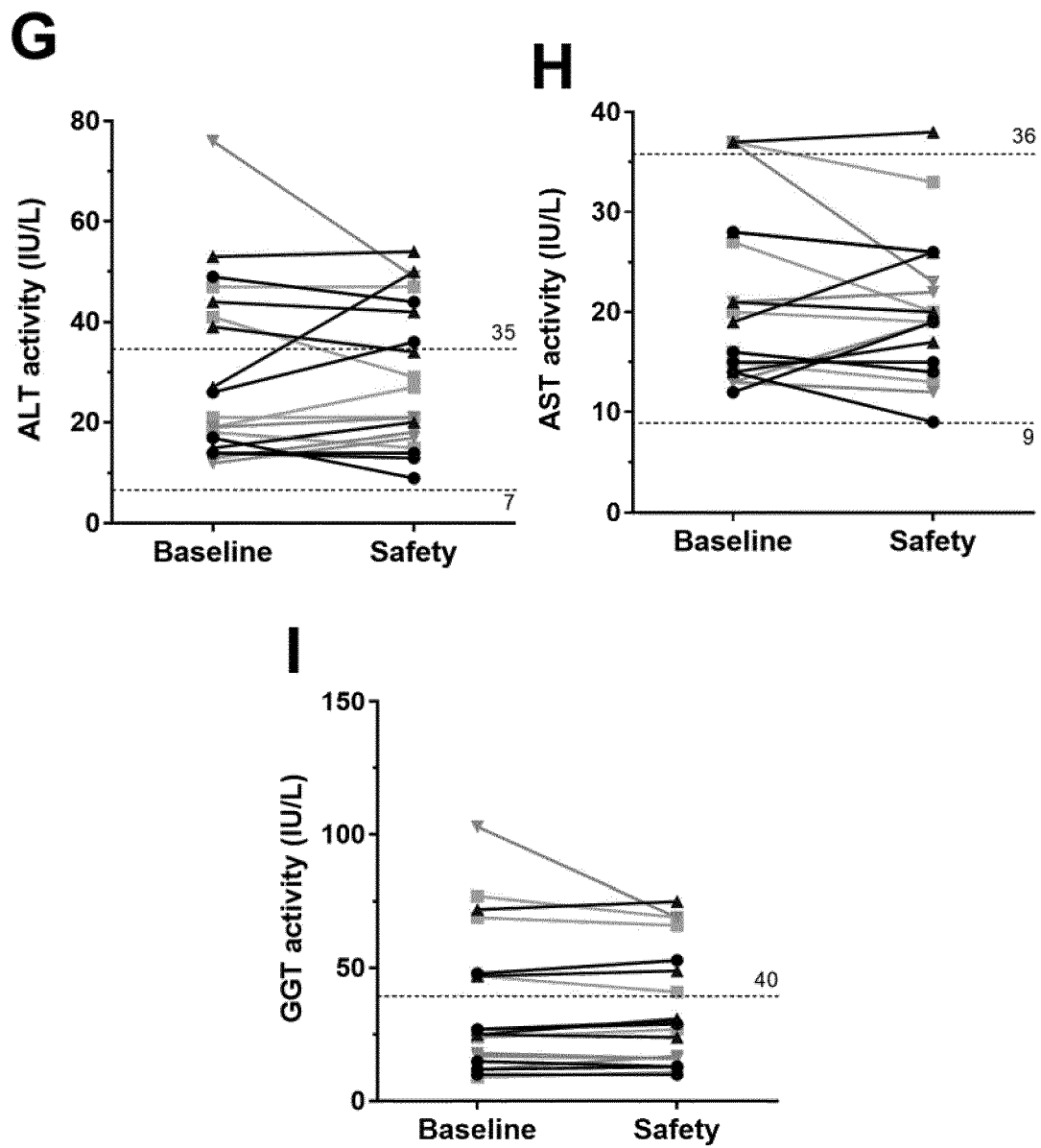
FIG. 14G-I

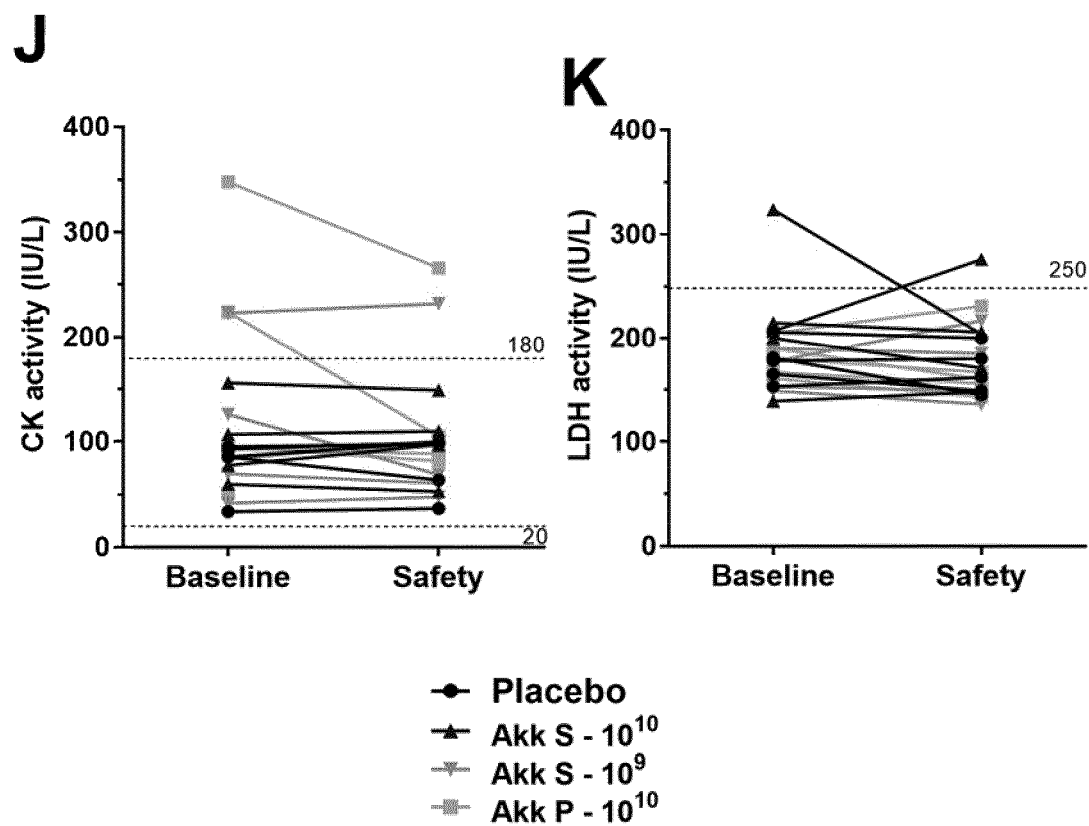
FIG. 14J-K

USE OF PASTEURIZED *AKKERMANSIA* FOR TREATING METABOLIC DISORDERS

RELATED APPLICATIONS

This application is a 35 U.S.C. § 371 filing of International Patent Application No. PCT/EP2016/071327, filed Sep. 9, 2016, which claims priority to European Patent Application No. 15184758.9, filed Sep. 10, 2015, the entire disclosures of which are hereby incorporated herein by reference.

FIELD OF INVENTION

The present invention relates to the treatment of metabolic disorders, such as, for example, metabolic disorders related to overweight and obesity, such as, for example, Diabetes Mellitus or high cholesterol. The present invention more specifically relates to a composition comprising pasteurized *Akkermansia* spp. or fragments thereof for treating a metabolic disorder.

BACKGROUND OF INVENTION

Obesity is a worldwide problem, with an estimated number of obese adults of about 600 million. This epidemic of obesity is correlated with a great increase in the prevalence of obesity-related disorders, such as, for example, diabetes, hypertension, cardiac pathologies and liver diseases. Due to these highly disabling pathologies, obesity is currently considered in western countries as one of the most important public health problems. There is thus a real need of compositions and methods for treating or preventing obesity and/or obesity-related disorders.

Obesity and obesity-related diseases are associated with (i) metabolic dysfunctions (with an impact on glucose homeostasis and lipid metabolism for example); (ii) low grade inflammatory state associated to higher blood lipopolysaccharides (LPS) levels (also referred as metabolic endotoxemia); and (iii) impaired gut barrier function (i.e. increased gut permeability) leading to translocation of bacteria and/or microorganisms components into organs such as the liver or the adipose tissue. In order to treat obesity, impact on at least one, preferably 2 and more preferably 3 of these 3 factors is thus needed. These phenomena (i.e., intestinal inflammation, LPS and bacterial translocation) are also observed during inflammatory bowel diseases, such as for instance Crohn's diseases, colitis, ulcerative colitis, intestinal pain (e.g., colic) and other intestinal inflammatory diseases. Interestingly, both inflammatory bowel diseases and obesity-related diseases are associated with changes in the gut microbiota composition. Thus, reinforcing the gut barrier function is one of the major issues.

The human gut is colonized by a diverse, complex and dynamic community of microbes representing over 1000 different species, which continuously interact with the host (Zoetendal et al., 2008. *Gut.* 57(11):1605-1615; Rajilic-Stojanavic and de Vos, 2014. *FEMS Microbiol. Rev.* 38:996-1047). The homeostasis of the gut microbiota is dependent on host characteristics (age, gender, genetic background . . . ) and environmental conditions (stress, drugs, gastrointestinal surgery, infectious and toxic agents . . . ), but also on the day-to-day dietary changes.

It has been recently acknowledged that the intestinal microbiota is involved in a number of brain disorders, such as anxiety, autism (Hsiao et al., 2013. *Cell.* 155(7):1451-1463), Parkinson's disease (Scheperjans et al., 2015. *Mov. Disord.* 30(3):350-8), Alzheimer's disease (Harach et al., 2015. arXiv:1509.02273), and in multiple sclerosis (Berer et al., 2011. *Nature.* 479(7374):538-41).

Gut microbiota imbalance was also shown to be a risk factor for the development of cancers such as colorectal cancer (Zitvogel et al., 2015. *Sci. Transl. Med.* 7(271): 271ps1; Louis et al., 2014. *Nat. Rev. Microbiol.* 12(10):661-72).

Growing evidences also support the role of gut microbiota in the development of obesity and related disorders (Delzenne & Cani, 2011. *Annu. Rev. Nutr.* 31:15-31) and intestinal inflammation (Wlodarska et al., 2015. *Cell Host Microbe.* 17(5):577-91), or intestinal pain (for example, babies' colic) (de Weerth et al., 2013. *Pediatrics.* 131:e550). In all these cases (obesity, intestinal inflammation, colic), dysbiosis of the microbiota can further disrupt the crosstalk between organs and the integrity of the intestinal barrier leading to symptoms.

Therefore, treatment with products that target the gut microbiota appeared as promising therapeutic tools for treating obesity and related disorders. These products may consist of living microbes, such as in the case of most probiotics, or contain dead microbes or fragments thereof. In addition, these products may comprise substrates that are used by the gut microbiota, such as in the case of prebiotics, or contain compounds that change the balance of the intestinal microbiota, such as specific antimicrobial compounds.

For example, WO 2008/076696 describes the gut microbiota as a therapeutic target for treating obesity and related disorders. WO 2008/076696 specifically describes methods for altering the abundance of Bacteroidetes and/or Firmicutes in the gut of a subject, by administering antibiotics and/or probiotics to the subject.

Moreover, EP 2 030 623 relates to the prevention and/or treatment of metabolic disorders, such as, for example, obesity related disorders, by regulating the amount of Enterobacteria in the gut. EP 2 030 623 discloses reducing the amount of Enterobacteria in the gut by administering probiotic bacteria, such as, for example, *Bifidobacterium, Lactococcus, Streptococcus, Enterococcus* or *Lactobacillus*.

The patent application US 2012/083514 relates to infant cereals comprising non-replicating probiotic micro-organisms. US 2012/083514 describes three types of heat treatment: 140° C. for 15 seconds (ultra high temperature); 74° C., 90° C. and 120° C. for 15 seconds (high temperature short time); and 85° C. for 20 minutes (long time low temperature). However, it is shown in this patent application US 2012/083514 that the ratio IL12/IL10 strongly increases in bacteria submitted to heat treatment at 85° C. for 20 minutes. IL12 is a proinflammatory cytokine, while IL10 is an anti-inflammatory cytokine. US 2012/083514 thus demonstrates that a heat treatment at 85° C. for 20 minutes increases the inflammatory state of the subject and is therefore not recommended for treating inflammatory disorders. Meanwhile, US 2012/083514 demonstrates that bacteria have to be heated for a very short time (15 seconds) to present an anti-inflammatory profile.

Furthermore, the Applicant described that the gut microbiota is modified in prebiotic-treated obese mice (Everard et al., 2011 November *Diabetes.* 60(11):2775-86). Moreover, prebiotics (1) improve glucose and lipid metabolisms in obese and diabetic mice, (2) reduce plasma LPS and improve gut barrier function (e.g. reduction of inflammation) in obese mice, (3) induce an increased enteroendocrine L-cell number in obese and diabetic mice, and (4) improve leptin sensitivity and glucose homeostasis in diet-induced obese and diabetic mice.

The Applicant also described the use of *Akkermansia muciniphila* or fragments thereof for treating obesity and related disorders (WO 2014/076246). Moreover, the Applicant also disclosed a reduced abundance of *Akkermansia muciniphila* in the gut of patients suffering from ulcerative colitis (Rajilić-Stojanović M et al., 2013 March *Inflamm. Bowel Dis.* 19(3):481-8). In Crohn's disease mainly butyrate-producing bacteria were found to be depleted (Wlodarska et al., 2015. *Cell Host Microbe.* 17(5):577-91). However, it was shown that *Akkermansia muciniphila*, which produces the short chain fatty acids propionate and acetate, can also give rise to trophic chains that produce butyrate as end product from mucus. Butyrate is known to reduce pain sensation in the gut and, like acetate and propionate, is known to show immune signaling. Finally, it has been shown that addition of *Akkermansia muciniphila* increases the barrier function in a human cell line (Reunanen et al., 2015. *Appl. Environ. Microbiol.* 81(11):3655-62). Hence, it is very likely that *Akkermansia muciniphila* and its products may reduce intestinal pain and inflammation as well as reinforce the gut barrier in healthy human as well as in patients suffering from intestinal inflammatory diseases. This may not only apply to adults but also to infants, as reduced butyrate producers were associated with excessive crying in baby colic and atopic diseases in young infants (de Weerth et al., 2013. *Gut Microbes.* 4(5):416-21; Nylund et al., 2015. *Allergy.* 70(2):241-4).

However, here, the Applicant surprisingly showed that administration of pasteurized *Akkermansia muciniphila* is more efficient than non-pasteurized *Akkermansia muciniphila* to increase barrier function and treat metabolic dysfunctions associated with obesity and related disorders. The present invention thus relates to the use of pasteurized *Akkermansia muciniphila* or fragments thereof to increase barrier function and treating obesity and related disorders.

SUMMARY

The present invention relates to *Akkermansia muciniphila* or fragments thereof for use in treating a metabolic disorder in a subject in need thereof, wherein *Akkermansia muciniphila* is pasteurized. In one particular embodiment, *Akkermansia muciniphila* or fragments thereof is for use in treating obesity.

In one embodiment, *Akkermansia muciniphila* or fragments thereof is for use in treating a metabolic disorder, wherein said metabolic disorder is selected from the group comprising metabolic syndrome; insulin-deficiency or insulin-resistance related disorders; Diabetes Mellitus including Type 2 Diabetes; glucose intolerance; abnormal lipid metabolism; atherosclerosis; hypertension; pre-eclampsia; cardiac pathology; stroke; non-alcoholic fatty liver disease; hyperglycemia; hepatic steatosis; liver diseases including fibrosis associated with obesity and abnormal liver functions, more particularly changes in bile production and immunity; dyslipidemia; dysfunction of the immune system associated with overweight and obesity; inflammatory, immune and barrier function diseases, including inflammatory bowel disease, more particularly Crohn's disease and ulcerative colitis, and irritable bowel syndrome; cardiovascular diseases; high cholesterol; elevated triglycerides; asthma; sleep apnea; osteoarthritis; neuro-degeneration; gallbladder disease; syndrome X; atherogenic dyslipidemia and cancer.

The present invention also relates to *Akkermansia muciniphila* or fragments thereof for increasing energy expenditure of a subject, preferably without impacting the food intake of said subject, wherein *Akkermansia muciniphila* is pasteurized.

Another object of the invention is *Akkermansia muciniphila* or fragments thereof for increasing satiety in a subject, wherein *Akkermansia muciniphila* is pasteurized.

In one embodiment, *Akkermansia muciniphila* or fragments thereof for use as described hereinabove is orally administered.

In one embodiment, *Akkermansia muciniphila* or fragments thereof for use as described hereinabove is administered to the subject in an amount ranging from about $1.10^4$ to about $1.10^{12}$ cells, more preferably from about $1.10^5$ to about $1.10^{11}$ cells, and even more preferably from about $1.10^6$ to about $1.10^{10}$ cells.

In one embodiment of the invention, *Akkermansia muciniphila* or fragments thereof for use as described hereinabove is administered at least three times a week.

In one embodiment, *Akkermansia muciniphila* or fragments thereof for use as described hereinabove is co-administered with another probiotic strain and/or another bacteria and/or microorganisms with beneficial effects and/or with one or more prebiotics.

The present invention also relates to a composition for use for treating a metabolic disorder or for increasing energy expenditure of a subject or for increasing satiety in a subject comprising *Akkermansia muciniphila* or fragments thereof as described hereinabove in association with an excipient.

In one embodiment, said composition for use is a nutritional composition. In one embodiment, said composition for use is orally administered.

Another object of the invention is a pharmaceutical composition for treating a metabolic disorder or for increasing energy expenditure of a subject or for increasing satiety in a subject comprising *Akkermansia muciniphila* or fragments thereof as described hereinabove in association with a pharmaceutically acceptable vehicle.

The present invention further relates to a medicament for treating a metabolic disorder or for increasing energy expenditure of a subject or for increasing satiety in a subject comprising *Akkermansia muciniphila* or fragments thereof as described hereinabove.

The present invention also relates to the use of *Akkermansia muciniphila* or fragments thereof for promoting weight loss in a subject in need thereof, wherein *Akkermansia muciniphila* is pasteurized.

Another object of the invention is a cosmetic composition comprising *Akkermansia muciniphila* or fragments thereof for promoting weight loss in a subject in need thereof, wherein *Akkermansia muciniphila* is pasteurized.

Definitions

In the present invention, the following terms have the following meanings:

"Treatment" means preventing (i.e. keeping from happening), reducing or alleviating at least one adverse effect or symptom of a disease, disorder or condition. This term thus refers to both therapeutic treatment and prophylactic or preventative measures; wherein the object is to prevent or slow down (lessen) the targeted pathologic condition or disorder. In one embodiment of the invention, those in need of treatment include those already with the disorder as well as those prone to have the disorder or those in whom the disorder is to be prevented.

"Effective amount" refers to level or amount of agent that is aimed at, without causing significant negative or adverse side effects to the target, (1) delaying or preventing the onset of a metabolic disorder; (2) slowing down or stopping the progression, aggravation, or deterioration of one or more symptoms of the metabolic disorder; (3) bringing about ameliorations of the symptoms of the metabolic disorder; (4) reducing the severity or incidence of the metabolic disorder; (5) curing the metabolic disorder; or (6) restoring the normal amount and/or proportion of *Akkermansia muciniphila* in the gut of the subject to be treated. An effective amount may be administered prior to the onset of a metabolic disorder, for a prophylactic or preventive action. Alternatively or additionally, the effective amount may be administered after initiation of the metabolic disorder, for a therapeutic action.

"*Akkermansia muciniphila*" refers to the mucin-degrading bacteria identified by Derrien (Derrien et al., 2004. *Int. J. Syst. Evol. Microbiol.* 54:1469-1476). Cells are oval-shaped, non-motile and stain Gram-negative. *Akkermansia muciniphila* may also be referred as *Akkermansia* spp. or *Akkermansia*-like bacteria. It belongs to the Chlamydiae/Verrucomicrobia group; Verrucomicrobia phylum. If the taxonomy should change, the skilled artisan would know how to adapt the changes in the taxonomy to deduce the strains that could be used in the present invention. Moreover, the complete genome of *Akkermansia muciniphila* has been determined by the Applicant (van Passel et al., 2011. *PLoS One.* 6(3): e16876). It is generally accepted that strains with a nucleotide similarity as experimentally determined by DNA-DNA hybridization of about 70% can be considered as the same species—this corresponds to an average nucleotide identity (ANI) of approximately 95% (Goris et al., 2007. *Int. J. Syst. Evol. Microbiol.* 57:81-91).

"Pasteurized *Akkermansia muciniphila*" refers to *Akkermansia muciniphila* submitted to a heating treatment. In one embodiment, pasteurized *Akkermansia muciniphila* refers to *Akkermansia muciniphila* which was heated at a temperature from 50° C. to 100° C. for at least 10 minutes.

"Probiotics" refers to microbial cell preparations (such as, for example, living microbial cells) which, when administered in an effective amount, provide a beneficial effect on the health or well-being of a subject. By definition, all probiotics have a proven non-pathogenic character. In one embodiment, these health benefits are associated with improving the balance of human or animal microbiota in the gastrointestinal tract, and/or restoring normal microbiota.

"Prebiotic" refers to a substance, such as, for example, a substance which may not be digested by humans, but which modulates composition and/or activity of the gut microbiota through its metabolization by microorganisms in the gut, thus conferring a beneficial physiological effect on the host.

"Subject" refers to an animal, preferably a mammal, more preferably a human. In one embodiment, the subject is a male. In another embodiment, the subject is a female. In one embodiment of the invention, a subject may also refer to a pet, such as, for example, a dog, a cat, a guinea pig, a hamster, a rat, a mouse, a ferret, a rabbit and the like.

"Overweight" refers to a subject situation wherein said subject has a Body Mass Index (BMI) ranging from 25 to 30. As used herein, BMI is defined as the individual's body mass (in kg) divided by the square of his/her height (in meter).

"Obesity" refers to a subject situation wherein said subject has a BMI superior or equal to 30.

"About" preceding a figure means plus or less 20%, preferably 10% of the value of said figure.

"Fragment" may refer to cellular components, metabolites, secreted molecules and compounds resulting from the metabolism of pasteurized *Akkermansia muciniphila* and the like. Fragments may be obtained, for example, by recovering the supernatant of a culture of *Akkermansia muciniphila* after pasteurization or by extracting cell components or cell fractions, metabolites or secreted compounds from a culture of *Akkermansia muciniphila* after pasteurization. The term fragment may also refer to a degradation product. A fragment may correspond to a component in the isolated form or to any mixture of one or more components derived from pasteurized *Akkermansia muciniphila*. In one embodiment, a fragment may correspond to one or more of such a components present in pasteurized *Akkermansia muciniphila* that is produced in another way, such as using recombinant DNA technology, in a microbial host or in any other (bio) synthetic process.

"Metabolic disorder" refers to disorders, diseases and conditions caused or characterized by abnormal weight gain, energy use or consumption, altered responses to ingested or endogenous nutrients, energy sources, hormones or other signaling molecules within the body or altered metabolism of carbohydrates, lipids, proteins, nucleic acids or a combination thereof. A metabolic disorder may be associated with either a deficiency or an excess in a metabolic pathway resulting in an imbalance in metabolism of carbohydrates, lipids, proteins and/or nucleic acids. Examples of metabolic disorders include, but are not limited to, metabolic syndrome, insulin-deficiency or insulin-resistance related disorders, Diabetes Mellitus (such as, for example, Type 2 Diabetes), glucose intolerance, abnormal lipid metabolism, atherosclerosis, hypertension, pre-eclampsia, cardiac pathology, stroke, non-alcoholic fatty liver disease, hyperglycemia, hepatic steatosis from different etiology, dyslipidemia, dysfunction of the immune system associated with overweight and obesity, cardiovascular diseases, high cholesterol, elevated triglycerides, asthma, sleep apnea, osteoarthritis, neuro-degeneration, gallbladder disease, syndrome X, inflammatory and immune disorders, atherogenic dyslipidemia and cancer.

DETAILED DESCRIPTION

The Applicant herein shows that the beneficial effects on metabolism observed after pasteurized *Akkermansia muciniphila* administration are more important than after non-pasteurized *Akkermansia muciniphila* administration (see Examples).

Therefore, this invention relates to pasteurized *Akkermansia muciniphila* or a fragment thereof for treating, or for use in treating, metabolic disorders in a subject in need thereof.

As used herein, a metabolic disorder is a disorder related to an altered metabolic homeostasis, such as, for example, an altered glucose or lipid homeostasis.

In one embodiment of the invention, said metabolic disorder is obesity.

Examples of other metabolic disorders include, but are not limited to, metabolic syndrome, insulin-deficiency or insulin-resistance related disorders, Diabetes Mellitus (such as, for example, Type 2 Diabetes), glucose intolerance, abnormal lipid metabolism, atherosclerosis, hypertension, pre-eclampsia, cardiac pathology, stroke, non-alcoholic fatty liver disease, hyperglycemia, hepatic steatosis, dyslipidemia, dysfunction of the immune system associated with overweight and obesity, liver diseases (such as, for example, fibrosis associated with obesity, or abnormal liver functions, including changes in bile production, immunity, and the like), inflammatory, immune and barrier function diseases (such as, for example, inflammatory bowel disease, including Crohn's disease and ulcerative colitis, and irritable bowel syndrome), cardiovascular diseases, high cholesterol, elevated triglycerides, asthma, sleep apnea, osteoarthritis, neuro-degeneration, gallbladder disease, syndrome X, inflammatory and immune disorders, atherogenic dyslipidemia and cancer.

In another embodiment, said metabolic disorder is an overweight and/or obesity related metabolic disorder, i.e. a metabolic disorder that may be associated to or caused by overweight and/or obesity. Examples of overweight and/or obesity related metabolic disorders include, but are not limited to metabolic syndrome, insulin-deficiency or insulin-resistance related disorders, Diabetes Mellitus (such as, for example, Type 2 Diabetes), glucose intolerance, abnormal lipid metabolism, atherosclerosis, hypertension, cardiac pathology, stroke, non-alcoholic fatty liver disease, hyperglycemia, hepatic steatosis, dyslipidemia, dysfunction of the immune system associated with overweight and obesity, cardiovascular diseases, high cholesterol, elevated triglycerides, asthma, sleep apnea, osteoarthritis, neuro-degeneration, gallbladder disease, syndrome X, inflammatory and immune disorders, atherogenic dyslipidemia and cancer.

In one embodiment, said metabolic disorder is Diabetes Mellitus, preferably Type 2 Diabetes. In another embodiment, said metabolic disorder is hypercholesterolemia (also known as high cholesterol). In one embodiment, hypercholesterolemia corresponds to a plasma cholesterol concentration superior or equal to 2 g/L or 5 mmol/L. In another embodiment, hypercholesterolemia corresponds to a ratio plasma concentration of total cholesterol: plasma concentration of HDL (high density lipoprotein cholesterol) superior or equal to 4.5:1, preferably 5:1.

As used herein, the term "pasteurized *Akkermansia muciniphila*" means *Akkermansia muciniphila* submitted to heating. In one embodiment, the pasteurized *Akkermansia muciniphila* of the invention was heated at a temperature from 50° C. to 100° C., preferably from 60° C. to 95° C., more preferably from 70° C. to 90° C. In one embodiment, the pasteurized *Akkermansia muciniphila* of the invention was heated at a temperature of 50, 51, 52, 53, 54, 55, 56, 57, 58 or 59° C. In another embodiment, the pasteurized *Akkermansia muciniphila* of the invention was heated at a temperature of 60, 61, 62, 63, 64, 65, 66, 67, 68 or 69° C. In yet another embodiment, the pasteurized *Akkermansia muciniphila* of the invention was heated at a temperature of 70, 71, 72, 73, 74, 75, 76, 77, 78 or 79° C. In yet another embodiment, the pasteurized *Akkermansia muciniphila* of the invention was heated at a temperature of 80, 81, 82, 83, 84, 85, 86, 87, 88 or 89° C. In yet another embodiment, the pasteurized *Akkermansia muciniphila* of the invention was heated at a temperature of 90, 91, 92, 93, 94, 95, 96, 97, 98, 99° C. or 100° C.

In one embodiment, the pasteurized *Akkermansia muciniphila* of the invention was not heated at a temperature superior to 100° C. In a particular embodiment, the pasteurized *Akkermansia muciniphila* of the invention was not heated at an ultra-high temperature, such as for example at a temperature of 110° C. to 140° C. In one embodiment, the pasteurized *Akkermansia muciniphila* of the invention was not heated at a temperature superior to 90° C. Accordingly, in one embodiment of the invention, *Akkermansia muciniphila* was not sterilized. Sterilization is a treatment intended to destroy, kill or inactivate all life forms and other biological agents. This includes microorganisms and their spores as well as viruses and prions. Unlike sterilization, pasteurization is not intended to kill all microorganisms but is usually applied to food with the aim to reduce the number of viable pathogens.

In one embodiment of the invention, the pasteurized *Akkermansia muciniphila* was heated for at least 10 minutes. In another embodiment of the invention, the pasteurized *Akkermansia muciniphila* was heated for at least 15, 20, 25, 30, 35 or 45 minutes. In one embodiment, the pasteurized *Akkermansia muciniphila* of the invention was heated for a period from 10 to 45 minutes.

In one embodiment, the pasteurized *Akkermansia muciniphila* was not heated for a short time. In a particular embodiment, the pasteurized *Akkermansia muciniphila* was not heated for a time of 1 to 30 seconds, of 1 to 60 seconds, of 1 to 90 seconds or of 1 to 120 seconds. In a preferred embodiment, the pasteurized *Akkermansia muciniphila* was not heated for a time of less than 1 minute, preferably for a time of less than 5, 6, 7, 8, or 9 minutes.

In one embodiment, the pasteurized *Akkermansia muciniphila* was heated at a temperature from 50° C. to 100° C. for at least 10 minutes. In a particular embodiment, the pasteurized *Akkermansia muciniphila* of the invention was heated to 60° C. for 20 or 30 minutes. In another particular embodiment, the pasteurized *Akkermansia muciniphila* of the invention was heated to 70° C. for 20 or 30 minutes. In another particular embodiment, the pasteurized *Akkermansia muciniphila* of the invention was heated to 80° C. for 20 or 30 minutes. In another particular embodiment, the pasteurized *Akkermansia muciniphila* of the invention was heated to 90° C. for 20 or 30 minutes.

In a particular embodiment, the pasteurized *Akkermansia muciniphila* was not heated at a temperature superior to 110° C. for about 1 to 120 seconds. In another particular embodiment, the pasteurized *Akkermansia muciniphila* was not heated at a temperature superior to 100° C. for about 1 to 120 seconds. In another particular embodiment, the pasteurized *Akkermansia muciniphila* was not heated at a temperature superior to 90° C. for about 1 to 120 seconds.

According to one embodiment, pasteurized *Akkermansia muciniphila* of the invention are non-viable cells. As used herein, "non-viable cells" means cells that are not able to proliferate. Measurement of cell viability and proliferation may be any method known to one skilled in the art. For example, cell viability and proliferation may be assessed by spreading a solution containing pasteurized *Akkermansia muciniphila* across a petri dish or using any other culture methods and counting the number of clones or optical density after a determined time of incubation in optimal growth conditions. Moreover, it is also possible to determine the number of cells, including viable as well as non-viable cells at least as the integrity of the cells is not compromised, by microscopic observation. While phase-contrast microscopy is a well-known method to do so, the microbial cells can be further visualized by specific staining with dyes, fluorescent probes or antibodies. This allows facilitation of microscopic observations while the number of stained cells can be also be counted by flow cytometry. Examples to visualize or counts cells of *Akkermansia muciniphila* have been provided by Derrien et al. (2008. *Appl. Environ. Microbiol.* 74:1646-8), Derrien et al. (2011. *Frontiers Microbiol.* 2:166-175) or Reunanen et al. (2015. *Appl. Environ. Microbiol.* 81(11):3655-62).

In one embodiment, pasteurized *Akkermansia muciniphila* or a fragment thereof is substantially purified. As used herein, the term "substantially purified" means that pasteurized *Akkermansia muciniphila* or fragment thereof is comprised in a sample wherein it represents at least about 50%, preferably at least about 60, 70, 80, 85, 90, 95, 99% or more of the bacterial strains or fragment thereof of said sample.

The present invention also relates to a composition comprising an effective amount of pasteurized *Akkermansia muciniphila* or a fragment thereof for treating, or for use in treating, a metabolic disorder.

In one embodiment of the invention, the effective amount of pasteurized *Akkermansia muciniphila* corresponds to the amount of the bacteria sufficient for restoring a normal amount and/or proportion of *Akkermansia muciniphila* within the gut of the subject. In one embodiment of the invention, the normal amount and/or proportion of *Akkermansia muciniphila* corresponds to the amount, and/or to the proportion of *Akkermansia muciniphila* present in the gut of a healthy subject.

As used herein, the term "healthy subject" is used to define a subject which is not affected by the disease to be treated. For example, if pasteurized *Akkermansia muciniphila* or a fragment thereof is used for treating obesity, the healthy subject is not affected by obesity. Preferably, the healthy subject shares common characteristics with the subject to be treated, such as, for example, same gender, age, sex, diet, drugs intake or geolocation.

In one embodiment of the invention, the normal proportion of *Akkermansia muciniphila* in the gut ranges from about 0.1% to about 10% (in number of *Akkermansia muciniphila* cells to the total number of bacteria cells of the gut), preferably from about 0.3% to about 5%, more preferably from about 1% to about 3%.

In one embodiment, the effective amount of pasteurized *Akkermansia muciniphila* of the invention corresponds to an amount of *Akkermansia muciniphila* before the step of pasteurization ranging from about $1.10^2$ to about $1.10^{15}$ cfu, preferably from about $1.10^4$ to about $1.10^{12}$ cfu, more preferably from about $1.10^5$ to about $1.10^{10}$ cfu, and even more preferably from about $1.10^6$ to about $1.10^9$ cfu, wherein cfu stands for "colony forming unit".

In another embodiment of the invention, the effective amount of pasteurized *Akkermansia muciniphila* corresponds to an amount of *Akkermansia muciniphila* before the step of pasteurization ranging from about $1.10^6$ to about $1.10^{10}$ cfu, preferably from about $1.10^8$ to about $1.10^{10}$ cfu, more preferably from about $1.10^9$ to about $1.10^{10}$ cfu.

In another embodiment of the invention, the effective amount of pasteurized *Akkermansia muciniphila* corresponds to an amount of *Akkermansia muciniphila* before the step of pasteurization ranging from about $1.10^6$ to about $1.10^{11}$ cfu, preferably from about $1.10^8$ to about $1.10^{11}$ cfu, more preferably from about $1.10^{10}$ to about $1.10^{11}$ cfu.

In one embodiment, the effective amount of pasteurized *Akkermansia muciniphila* of the invention ranges from about $1.10^2$ to about $1.10^{15}$ cells, preferably from about $1.10^4$ to about $1.10^{12}$ cells, more preferably from about $1.10^5$ to about $1.10^{10}$ cells, and even more preferably from about $1.10^6$ to about $1.10^9$ cells.

In another embodiment of the invention, the effective amount of pasteurized *Akkermansia muciniphila* ranges from about $1.10^6$ to about $1.10^{10}$ cells, preferably from about $1.10^8$ to about $1.10^{10}$ cells, more preferably from about $1.10^9$ to about $1.10^{10}$ cells.

In another embodiment of the invention, the effective amount of pasteurized *Akkermansia muciniphila* ranges from about $1.10^6$ to about $1.10^{11}$ cells, preferably from about $1.10^8$ to about $1.10^{11}$ cells, more preferably from about $1.10^{10}$ to about $1.10^{11}$ cells.

In one embodiment of the invention, the effective amount of a fragment of pasteurized *Akkermansia muciniphila* corresponds to an amount of *Akkermansia muciniphila* before the step of pasteurization ranging from fragments derived from about $1.10^2$ to about $1.10^{15}$ cfu, preferably from about $1.10^4$ to about $1.10^{12}$ cfu, more preferably from about $1.10^5$ to about $1.10^{10}$ cfu, and even more preferably from about $1.10^6$ to about $1.10^9$ cfu, wherein cfu stands for "colony forming unit".

In another embodiment of the invention, the effective amount of a fragment of pasteurized *Akkermansia muciniphila* corresponds to an amount of *Akkermansia muciniphila* before the step of pasteurization ranging from fragments derived from about $1.10^6$ to about $1.10^{10}$ cfu, preferably from about $1.10^8$ to about $1.10^{10}$ cfu, more preferably from about $1.10^9$ to about $1.10^{10}$ cfu.

In another embodiment of the invention, the effective amount of a fragment of pasteurized *Akkermansia muciniphila* corresponds to an amount of *Akkermansia muciniphila* before the step of pasteurization ranging from fragments derived from about $1.10^6$ to about $1.10^{11}$ cfu, preferably from about $1.10^8$ to about $1.10^{11}$ cfu, more preferably from about $1.10^{10}$ to about $1.10^{11}$ cfu.

In one embodiment of the invention, the effective amount of a fragment of pasteurized *Akkermansia muciniphila* ranges from fragments derived from about $1.10^2$ to about $1.10^{15}$ cells, preferably from about $1.10^4$ to about $1.10^{12}$ cells, more preferably from about $1.10^5$ to about $1.10^{10}$ cells, and even more preferably from about $1.10^6$ to about $1.10^9$ cells. In another embodiment of the invention, the effective amount of a fragment of pasteurized *Akkermansia muciniphila* ranges from fragments derived from about $1.10^6$ to about $1.10^{10}$ cells, preferably from about $1.10^8$ to about $1.10^{10}$ cells, more preferably from about $1.10^9$ to about $1.10^{10}$ cells.

In another embodiment of the invention, the effective amount of a fragment of pasteurized *Akkermansia muciniphila* ranges from fragments derived from about $1.10^6$ to about $1.10^{11}$ cells, preferably from about $1.10^8$ to about $1.10^{11}$ cells, more preferably from about $1.10^{10}$ to about $1.10^{11}$ cells.

In one embodiment of the invention, the composition of the invention comprises an amount of pasteurized *Akkermansia muciniphila* corresponding to an amount of *Akkermansia muciniphila* before the step of pasteurization ranging from about $1.10^2$ to about $1.10^{15}$ cfu/g of the composition, preferably from about $1.10^4$ to about $1.10^{12}$ cfu/g of the composition, more preferably from about $1.10^5$ to about $1.10^{10}$ cfu/g of the composition and even more preferably from about $1.10^6$ to about $1.10^9$ cfu/g of the composition.

In one embodiment of the invention, the composition of the invention comprises an amount of pasteurized *Akkermansia muciniphila* corresponding to an amount of *Akkermansia muciniphila* before the step of pasteurization ranging from about $1.10^2$ to about $1.10^{15}$ cfu/mL of the composition, preferably from about $1.10^4$ to about $1.10^{12}$ cfu/mL of the composition, more preferably from about $1.10^5$ to about $1.10^{10}$ cfu/mL of the composition and even more preferably from about $1.10^6$ to about $1.10^9$ cfu/mL of the composition.

In another embodiment of the invention, the composition of the invention comprises an amount of pasteurized *Akkermansia muciniphila* corresponding to an amount of *Akkermansia muciniphila* before the step of pasteurization ranging from about $1.10^6$ to about $1.10^{10}$ cfu/g or cfu/mL of the composition, preferably from about $1.10^8$ to about $1.10^{10}$ cfu/g or cfu/mL, more preferably from about $1.10^9$ to about $1.10^{10}$ cfu/g or cfu/mL.

In another embodiment of the invention, the composition of the invention comprises an amount of pasteurized *Akkermansia muciniphila* corresponding to an amount of *Akkermansia muciniphila* before the step of pasteurization ranging from about $1.10^6$ to about $1.10^{11}$ cfu/g or cfu/mL of the composition, preferably from about $1.10^8$ to about $1.10^{11}$ cfu/g or cfu/mL, more preferably from about $1.10^{10}$ to about $1.10^{11}$ cfu/g or cfu/mL.

In one embodiment of the invention, the composition of the invention comprises an amount of pasteurized *Akkermansia muciniphila* ranging from about $1.10^2$ to about $1.10^{15}$ cells/g of the composition, preferably from about $1.10^4$ to about $1.10^{12}$ cells/g of the composition, more preferably from about $1.10^5$ to about $1.10^{10}$ cells/g of the composition and even more preferably from about $1.10^6$ to about $1.10^9$ cells/g of the composition.

In one embodiment of the invention, the composition of the invention comprises an amount of pasteurized *Akkermansia muciniphila* ranging from about $1.10^2$ to about $1.10^{15}$ cells/mL of the composition, preferably from about $1.10^4$ to about $1.10^{12}$ cells/mL of the composition, more preferably from about $1.10^5$ to about $1.10^{10}$ cells/mL of the composition and even more preferably from about $1.10^6$ to about $1.10^9$ cells/mL of the composition.

In another embodiment of the invention, the composition of the invention comprises an amount of pasteurized *Akkermansia muciniphila* ranging from about $1.10^6$ to about $1.10^{10}$ cells/g or cells/mL of the composition, preferably from about $1.10^8$ to about $1.10^{10}$ cells/g or cells/mL, more preferably from about $1.10^9$ to about $1.10^{10}$ cells/g or cells/mL.

In another embodiment of the invention, the composition of the invention comprises an amount of pasteurized *Akkermansia muciniphila* ranging from about $1.10^6$ to about $1.10^{11}$ cells/g or cells/mL of the composition, preferably from about $1.10^8$ to about $1.10^{11}$ cells/g or cells/mL, more preferably from about $1.10^{10}$ to about $1.10^{11}$ cells/g or cells/mL.

In one embodiment of the invention, the composition of the invention comprises an amount of fragments of pasteurized *Akkermansia muciniphila* corresponding to an amount of *Akkermansia muciniphila* before the step of pasteurization ranging from fragments derived from about $1.10^2$ to about $1.10^{15}$ cfu/g or cfu/mL of the composition, preferably from about $1.10^4$ to about $1.10^{12}$ cfu/g or cfu/mL of the composition, more preferably from about $1.10^5$ to about $1.10^{10}$ cfu/g or cfu/mL of the composition and even more preferably from about $1.10^6$ to about $1.10^9$ cfu/g or cfu/mL of the composition.

In another embodiment of the invention, the composition of the invention comprises an amount of fragments of pasteurized *Akkermansia muciniphila* corresponding to an amount of *Akkermansia muciniphila* before the step of pasteurization ranging from fragments derived from about $1.10^6$ to about $1.10^{10}$ cfu/g or cfu/mL of the composition, preferably from about $1.10^8$ to about $1.10^{10}$ cfu/g or cfu/mL, more preferably from about $1.10^9$ to about $1.10^{10}$ cfu/g or cfu/mL.

In another embodiment of the invention, the composition of the invention comprises an amount of fragments of pasteurized *Akkermansia muciniphila* corresponding to an amount of *Akkermansia muciniphila* before the step of pasteurization ranging from fragments derived from about $1.10^6$ to about $1.10^{11}$ cfu/g or cfu/mL of the composition, preferably from about $1.10^8$ to about $1.10^{11}$ cfu/g or cfu/mL, more preferably from about $1.10^{10}$ to about $1.10^{11}$ cfu/g or cfu/mL.

In one embodiment of the invention, the composition of the invention comprises an amount of fragments of pasteurized *Akkermansia muciniphila* ranging from fragments derived from about $1.10^2$ to about $1.10^{15}$ cells/g or cells/mL of the composition, preferably from about $1.10^4$ to about $1.10^{12}$ cells/g or cells/mL of the composition, more preferably from about $1.10^5$ to about $1.10^{10}$ cells/g or cells/mL of the composition and even more preferably from about $1.10^6$ to about $1.10^9$ cells/g or cells/mL of the composition.

In another embodiment of the invention, the composition of the invention comprises an amount of fragments of pasteurized *Akkermansia muciniphila* ranging from fragments derived from about $1.10^6$ to about $1.10^{10}$ cells/g or cells/mL of the composition, preferably from about $1.10^8$ to about $1.10^{10}$ cells/g or cells/mL, more preferably from about $1.10^9$ to about $1.10^{10}$ cells/g or cells/mL.

In another embodiment of the invention, the composition of the invention comprises an amount of fragments of pasteurized *Akkermansia muciniphila* ranging from fragments derived from about $1.10^6$ to about $1.10^{11}$ cells/g or cells/mL of the composition, preferably from about $1.10^8$ to about $1.10^{11}$ cells/g or cells/mL, more preferably from about $1.10^{10}$ to about $1.10^{11}$ cells/g or cells/mL.

The present invention also relates to a pharmaceutical composition comprising an effective amount of pasteurized *Akkermansia muciniphila* or a fragment thereof and at least one pharmaceutically acceptable excipient. In one embodiment of the invention, the pharmaceutical composition of the invention is for treating or preventing a metabolic disorder. In another embodiment of the invention, the pharmaceutical composition is for restoring a normal proportion of *Akkermansia muciniphila* or increasing the abundance of any active compounds of *Akkermansia muciniphila* in the gut of a subject in need thereof.

As used herein the term "pharmaceutically acceptable excipient" refers to an excipient that does not produce an adverse, allergic or other untoward reaction when administered to an animal, preferably a human. It may include any and all solvents, dispersion media, coatings, isotonic and absorption delaying agents and the like. For human administration, preparations should meet sterility, pyrogenicity, general safety and purity standards as required by FDA Office of Biologics standards.

The present invention also relates to a medicament comprising an effective amount of pasteurized *Akkermansia muciniphila* or a fragment thereof. In one embodiment of the invention, the medicament of the invention is for treating or preventing a metabolic disorder. In another embodiment of the invention, the medicament is for restoring a normal proportion of *Akkermansia muciniphila* in the gut of a subject in need thereof.

The present invention also relates to a method for treating or preventing a metabolic disorder in a subject in need thereof, wherein said method comprises administering an effective amount of pasteurized *Akkermansia muciniphila* or a fragment thereof to the subject.

Another object of the invention is a method for restoring a normal proportion of *Akkermansia muciniphila*, fragments or other active compounds of *Akkermansia muciniphila* in the gut of a subject in need thereof, wherein said method comprises administering an effective amount of pasteurized *Akkermansia muciniphila* or a fragment thereof to the subject.

In one embodiment, the method of the invention comprises administering an effective amount of the composition, of the pharmaceutical composition or of the medicament of the invention to the subject.

In one embodiment of the invention, pasteurized *Akkermansia muciniphila* or a fragment thereof, or the composition, pharmaceutical composition or medicament is administered at least once a week, preferably at least twice a week, more preferably at least three times a week, and even more preferably at least four times a week. In another embodiment, pasteurized *Akkermansia muciniphila* or a fragment thereof, or the composition, pharmaceutical composition or medicament is administered at least once a day, and preferably at least twice a day.

In one embodiment, pasteurized *Akkermansia muciniphila* or a fragment thereof, or the composition, pharmaceutical composition or medicament of the invention is administered during 1 week, preferably during 2, 3, 4, 5, 6, 7 or 8 weeks or more.

In one embodiment, pasteurized *Akkermansia muciniphila* or a fragment thereof, or the composition, pharmaceutical composition or medicament of the invention is administered for a period that lasts until the desired outcome is achieved (e.g., weight loss, metabolic disorder treatment, decrease of cholesterol plasma level . . . ).

In one embodiment, the administration of pasteurized *Akkermansia muciniphila* or a fragment thereof, or the composition, pharmaceutical composition or medicament of the invention is permanent, i.e. is not limited in time.

In one embodiment of the invention, the daily amount of pasteurized *Akkermansia muciniphila* administered per day corresponds to an amount of *Akkermansia muciniphila* before the step of pasteurization ranging from $1.10^2$ to about $1.10^{15}$ cfu/day, preferably from about $1.10^4$ to about $1.10^{12}$ cfu/day, more preferably from about $1.10^5$ to about $1.10^{10}$ cfu/day and even more preferably from about $1.10^6$ to about $1.10^9$ cfu/day.

In another embodiment of the invention, the daily amount of pasteurized *Akkermansia muciniphila* administered per day corresponds to an amount of *Akkermansia muciniphila* before the step of pasteurization ranging from $1.10^6$ to about $1.10^{10}$ cfu/day, preferably from about $1.10^8$ to about $1.10^{10}$ cfu/day, more preferably from about $1.10^9$ to about $1.10^{10}$ cfu/day.

In another embodiment of the invention, the daily amount of pasteurized *Akkermansia muciniphila* administered per day corresponds to an amount of *Akkermansia muciniphila* before the step of pasteurization ranging from $1.10^6$ to about $1.10^{11}$ cfu/day, preferably from about $1.10^8$ to about $1.10^{11}$ cfu/day, more preferably from about $1.10^{10}$ to about $1.10^{11}$ cfu/day.

In one embodiment of the invention, the daily amount of pasteurized *Akkermansia muciniphila* administered per day ranges from $1.10^2$ to about $1.10^{15}$ cells/day, preferably from about $1.10^4$ to about $1.10^{12}$ cells/day, more preferably from about $1.10^5$ to about $1.10^{10}$ cells/day and even more preferably from about $1.10^6$ to about $1.10^9$ cells/day.

In another embodiment of the invention, the daily amount of pasteurized *Akkermansia muciniphila* administered per day ranges from $1.10^6$ to about $1.10^{10}$ cells/day, preferably from about $1.10^8$ to about $1.10^{10}$ cells/day, more preferably from about $1.10^9$ to about $1.10^{10}$ cells/day.

In another embodiment of the invention, the daily amount of pasteurized *Akkermansia muciniphila* administered per day ranges from $1.10^6$ to about $1.10^{11}$ cells/day, preferably from about $1.10^8$ to about $1.10^{11}$ cells/day, more preferably from about $1.10^{10}$ to about $1.10^{11}$ cells/day.

In one embodiment of the invention, the daily amount of fragments of pasteurized *Akkermansia muciniphila* administered per day corresponds to an amount of *Akkermansia muciniphila* before the step of pasteurization ranging from fragments derived from $1.10^2$ to about $1.10^{15}$ cfu/day, preferably from about $1.10^4$ to about $1.10^{12}$ cfu/day, more preferably from about $1.10^5$ to about $1.10^{10}$ cfu/day and even more preferably from about $1.10^6$ to about $1.10^9$ cfu/day.

In another embodiment of the invention, the daily amount of fragments of pasteurized *Akkermansia muciniphila* administered per day corresponds to an amount of *Akkermansia muciniphila* before the step of pasteurization ranging from fragments derived from $1.10^6$ to about $1.10^{10}$ cfu/day, preferably from about $1.10^8$ to about $1.10^{10}$ cfu/day, more preferably from about $1.10^9$ to about $1.10^{10}$ cfu/day.

In another embodiment of the invention, the daily amount of fragments of pasteurized *Akkermansia muciniphila* administered per day corresponds to an amount of *Akkermansia muciniphila* before the step of pasteurization ranging from fragments derived from $1.10^6$ to about $1.10^{11}$ cfu/day, preferably from about $1.10^8$ to about $1.10^{11}$ cfu/day, more preferably from about $1.10^{10}$ to about $1.10^{11}$ cfu/day.

In one embodiment of the invention, the daily amount of fragments of pasteurized *Akkermansia muciniphila* administered per day ranges from fragments derived from $1.10^2$ to about $1.10^{15}$ cells/day, preferably from about $1.10^4$ to about $1.10^{12}$ cells/day, more preferably from about $1.10^5$ to about $1.10^{10}$ cells/day and even more preferably from about $1.10^6$ to about $1.10^9$ cells/day.

In another embodiment of the invention, the daily amount of fragments of pasteurized *Akkermansia muciniphila* administered per day ranges from fragments derived from $1.10^6$ to about $1.10^{10}$ cells/day, preferably from about $1.10^8$ to about $1.10^{10}$ cells/day, more preferably from about $1.10^9$ to about $1.10^{10}$ cells/day.

In another embodiment of the invention, the daily amount of fragments of pasteurized *Akkermansia muciniphila* administered per day ranges from fragments derived from $1.10^6$ to about $1.10^{11}$ cells/day, preferably from about $1.10^8$ to about $1.10^{11}$ cells/day, more preferably from about $1.10^{10}$ to about $1.10^{11}$ cells/day.

In one embodiment of the invention, the subject is overweight. In another embodiment, the subject is obese.

In one embodiment of the invention, the subject is diagnosed with a metabolic disorder, such as, for example, with an overweight and/or obesity related metabolic disorder. In one embodiment of the invention, the subject is diagnosed with a metabolic disorder, such as, for example, with a normal weight and/or impaired fasting glucose and/or hypertriglyceridemia and/or any related metabolic disorder or cardiovascular risk factor.

In another embodiment, the subject is at risk of developing a metabolic disorder, such as, for example, an overweight and/or obesity related metabolic disorder. In one embodiment, said risk is related to the fact that the subject is overweight or obese. In another embodiment, said risk corresponds to a predisposition, such as, for example, a familial predisposition to a metabolic disorder, such as, for example, to an overweight and/or obesity related metabolic disorder.

In one embodiment of the invention, the subject presents a deregulation of the gut microbiota composition. Preferably, the gut microbiota of said subject is depleted in *Akkermansia muciniphila* strains. In one embodiment, the proportion of *Akkermansia muciniphila* in the gut of the subject is inferior to 1%, preferably inferior to 0.5%, more preferably inferior to 0.1%, in number of *Akkermansia muciniphila* cells to the total number of bacterial cells in the gut.

The present invention also relates to the cosmetic use of pasteurized *Akkermansia muciniphila* or a fragment thereof for promoting weight loss in a subject.

Another object of the invention is thus a cosmetic composition comprising a cosmetically effective amount of pasteurized *Akkermansia muciniphila* or a fragment thereof, and the use thereof for promoting weight loss in a subject. As used herein, a "cosmetically effective amount" refers to the amount of a cosmetic composition necessary and sufficient for promoting a cosmetic effect, such as, for example, for inducing weight loss in a subject.

The present invention also relates to a method for promoting weight loss in a subject in need thereof, wherein said method comprises administering a cosmetically effective amount of pasteurized *Akkermansia muciniphila* or a fragment thereof to said subject.

In one embodiment, the method of the invention comprises administering a cosmetically effective amount of the composition or of the cosmetic composition of the invention to the subject.

In one embodiment of the invention, the cosmetically effective amount of pasteurized *Akkermansia muciniphila* corresponds to an amount of *Akkermansia muciniphila* before the step of pasteurization ranging from about $1.10^2$ to about $1.10^{15}$ cfu, preferably from about $1.10^4$ to about $1.10^{12}$ cfu, more preferably from about $1.10^5$ to about $1.10^{10}$ cfu and even more preferably from about $1.10^6$ to about $1.10^9$ cfu.

In another embodiment of the invention, the cosmetically effective amount of pasteurized *Akkermansia muciniphila* corresponds to an amount of *Akkermansia muciniphila* before the step of pasteurization ranging from about $1.10^6$ to about $1.10^{10}$ cfu, preferably from about $1.10^8$ to about $1.10^{10}$ cfu, more preferably from about $1.10^9$ to about $1.10^{10}$ cfu.

In another embodiment of the invention, the cosmetically effective amount of pasteurized *Akkermansia muciniphila* corresponds to an amount of *Akkermansia muciniphila* before the step of pasteurization ranging from about $1.10^6$ to about $1.10^{11}$ cfu, preferably from about $1.10^8$ to about $1.10^{11}$ cfu, more preferably from about $1.10^{10}$ to about $1.10^{11}$ cfu.

In one embodiment of the invention, the cosmetically effective amount of pasteurized *Akkermansia muciniphila* ranges from about $1.10^2$ to about $1.10^{15}$ cells, preferably from about $1.10^4$ to about $1.10^{12}$ cells, more preferably from about $1.10^5$ to about $1.10^{10}$ cells and even more preferably from about $1.10^6$ to about $1.10^9$ cells.

In another embodiment of the invention, the cosmetically effective amount of pasteurized *Akkermansia muciniphila* ranges from about $1.10^6$ to about $1.10^{10}$ cells, preferably from about $1.10^8$ to about $1.10^{10}$ cells, more preferably from about $1.10^9$ to about $1.10^{10}$ cells.

In another embodiment of the invention, the cosmetically effective amount of pasteurized *Akkermansia muciniphila* ranges from about $1.10^6$ to about $1.10^{11}$ cells, preferably from about $1.10^8$ to about $1.10^{11}$ cells, more preferably from about $1.10^{10}$ to about $1.10^{11}$ cells.

In one embodiment of the invention, the cosmetically effective amount of fragments of pasteurized *Akkermansia muciniphila* corresponds to an amount of *Akkermansia muciniphila* before the step of pasteurization ranging from fragments derived from about $1.10^2$ to about $1.10^{15}$ cfu, preferably from about $1.10^4$ to about $1.10^{12}$ cfu, more preferably from about $1.10^5$ to about $1.10^{10}$ cfu and even more preferably from about $1.10^6$ to about $1.10^9$ cfu.

In another embodiment of the invention, the cosmetically effective amount of fragments of pasteurized *Akkermansia muciniphila* corresponds to an amount of *Akkermansia muciniphila* before the step of pasteurization ranging from fragments derived from about $1.10^6$ to about $1.10^{10}$ cfu, preferably from about $1.10^8$ to about $1.10^{10}$ cfu, more preferably from about $1.10^9$ to about $1.10^{10}$ cfu.

In another embodiment of the invention, the cosmetically effective amount of fragments of pasteurized *Akkermansia muciniphila* corresponds to an amount of *Akkermansia muciniphila* before the step of pasteurization ranging from fragments derived from about $1.10^6$ to about $1.10^{11}$ cfu, preferably from about $1.10^8$ to about $1.10^{11}$ cfu, more preferably from about $1.10^{10}$ to about $1.10^{11}$ cfu.

In one embodiment of the invention, the cosmetically effective amount of fragments of pasteurized *Akkermansia muciniphila* ranges from fragments derived from about $1.10^2$ to about $1.10^{15}$ cells, preferably from about $1.10^4$ to about $1.10^{12}$ cells, more preferably from about $1.10^5$ to about $1.10^{10}$ cells and even more preferably from about $1.10^6$ to about $1.10^9$ cells.

In another embodiment of the invention, the cosmetically effective amount of fragments of pasteurized *Akkermansia muciniphila* ranges from fragments derived from about $1.10^6$ to about $1.10^{10}$ cells, preferably from about $1.10^8$ to about $1.10^{10}$ cells, more preferably from about $1.10^9$ to about $1.10^{10}$ cells.

In another embodiment of the invention, the cosmetically effective amount of fragments of pasteurized *Akkermansia muciniphila* ranges from fragments derived from about $1.10^6$ to about $1.10^{11}$ cells, preferably from about $1.10^8$ to about $1.10^{11}$ cells, more preferably from about $1.10^{10}$ to about $1.10^{11}$ cells.

In one embodiment of the invention, pasteurized *Akkermansia muciniphila* or a fragment thereof, or the composition or cosmetic composition is administered at least once a week, preferably at least twice a week, more preferably at least three times a week, and even more preferably at least four times a week. In another embodiment, pasteurized *Akkermansia muciniphila* or a fragment thereof, or the composition or cosmetic composition is administered at least once a day, and preferably at least twice a day.

In one embodiment, pasteurized *Akkermansia muciniphila* or a fragment thereof, or the composition or cosmetic composition of the invention is administered during 1 week, preferably 2, 3, 4, 5, 6, 7 or 8 weeks or more.

In one embodiment, pasteurized *Akkermansia muciniphila* or a fragment thereof, or the composition or cosmetic composition of the invention is administered for a period that lasts until the desired outcome is achieved (e.g., weight loss . . . ).

In one embodiment, the administration of pasteurized *Akkermansia muciniphila* or a fragment thereof, or the composition or cosmetic composition of the invention is permanent, i.e. is not limited in time.

In one embodiment of the invention, the daily amount of pasteurized *Akkermansia muciniphila* administered per day corresponds to an amount of *Akkermansia muciniphila* before the step of pasteurization ranging from $1.10^2$ to about $1.10^{15}$ cfu/day, preferably from about $1.10^5$ to about $1.10^{12}$ cfu/day, more preferably from about $1.10^8$ to about $1.10^{10}$ cfu/day, and even more preferably from about $1.10^9$ to about $1.10^{10}$ cfu/day.

In another embodiment of the invention, the daily amount of pasteurized *Akkermansia muciniphila* administered per day corresponds to an amount of *Akkermansia muciniphila* before the step of pasteurization ranging from $1.10^6$ to about $1.10^{10}$ cfu/day, preferably from about $1.10^8$ to about $1.10^{10}$ cfu/day, more preferably from about $1.10^9$ to about $1.10^{10}$ cfu/day.

In another embodiment of the invention, the daily amount of pasteurized *Akkermansia muciniphila* administered per day corresponds to an amount of *Akkermansia muciniphila* before the step of pasteurization ranging from $1.10^6$ to about $1.10^{11}$ cfu/day, preferably from about $1.10^8$ to about $1.10^{11}$ cfu/day, more preferably from about $1.10^{10}$ to about $1.10^{11}$ cfu/day.

In one embodiment of the invention, the daily amount of pasteurized *Akkermansia muciniphila* administered per day ranges from $1.10^2$ to about $1.10^{15}$ cells/day, preferably from about $1.10^5$ to about $1.10^{12}$ cells/day, more preferably from about $1.10^8$ to about $1.10^{10}$ cells/day, and even more preferably from about $1.10^9$ to about $1.10^{10}$ cells/day.

In another embodiment of the invention, the daily amount of pasteurized *Akkermansia muciniphila* administered per day ranges from $1.10^6$ to about $1.10^{10}$ cells/day, preferably from about $1.10^8$ to about $1.10^{10}$ cells/day, more preferably from about $1.10^9$ to about $1.10^{10}$ cells/day.

In another embodiment of the invention, the daily amount of pasteurized *Akkermansia muciniphila* administered per day ranges from $1.10^6$ to about $1.10^{11}$ cells/day, preferably from about $1.10^8$ to about $1.10^{11}$ cells/day, more preferably from about $1.10^{10}$ to about $1.10^{11}$ cells/day.

In one embodiment of the invention, the daily amount of fragments of pasteurized *Akkermansia muciniphila* administered per day corresponds to an amount of *Akkermansia muciniphila* before the step of pasteurization ranging from fragments derived from about $1.10^2$ to about $1.10^{15}$ cfu/day, preferably from about $1.10^5$ to about $1.10^{12}$ cfu/day, more preferably from about $1.10^8$ to about $1.10^{10}$ cfu/day, and even more preferably from about $1.10^9$ to about $1.10^{10}$ cfu/day.

In another embodiment of the invention, the daily amount of fragments of pasteurized *Akkermansia muciniphila* administered per day corresponds to an amount of *Akkermansia muciniphila* before the step of pasteurization ranging from fragments derived from about $1.10^6$ to about $1.10^{10}$ cfu/day, preferably from about $1.10^8$ to about $1.10^{10}$ cfu/day, more preferably from about $1.10^9$ to about $1.10^{10}$ cfu/day.

In another embodiment of the invention, the daily amount of fragments of pasteurized *Akkermansia muciniphila* administered per day corresponds to an amount of *Akkermansia muciniphila* before the step of pasteurization ranging from fragments derived from about $1.10^6$ to about $1.10^{11}$ cfu/day, preferably from about $1.10^8$ to about $1.10^{11}$ cfu/day, more preferably from about $1.10^{10}$ to about $1.10^{11}$ cfu/day.

In one embodiment of the invention, the daily amount of fragments of pasteurized *Akkermansia muciniphila* administered per day ranges from fragments derived from about $1.10^2$ to about $1.10^{15}$ cells/day, preferably from about $1.10^5$ to about $1.10^{12}$ cells/day, more preferably from about $1.10^8$ to about $1.10^{10}$ cells/day, and even more preferably from about $1.10^9$ to about $1.10^{10}$ cells/day.

In another embodiment of the invention, the daily amount of fragments of pasteurized *Akkermansia muciniphila* administered per day ranges from fragments derived from about $1.10^6$ to about $1.10^{10}$ cells/day, preferably from about $1.10^8$ to about $1.10^{10}$ cells/day, more preferably from about $1.10^9$ to about $1.10^{10}$ cells/day.

In another embodiment of the invention, the daily amount of fragments of pasteurized *Akkermansia muciniphila* administered per day ranges from fragments derived from about $1.10^6$ to about $1.10^{11}$ cells/day, preferably from about $1.10^8$ to about $1.10^{11}$ cells/day, more preferably from about $1.10^{10}$ to about $1.10^{11}$ cells/day.

In one embodiment, said subject is not an obese subject. In another embodiment, said subject is overweight.

In one embodiment of the invention, the composition, the pharmaceutical composition, the cosmetic composition or the medicament further comprises additional probiotic strains or species, such as, for example, bacterial probiotic strains or species; prokaryotes probiotics other than bacteria; or fungal strains or species, preferably yeast strains or species. In one embodiment, said additional probiotic strains or species are selected from those naturally present in the gut of the subject, preferably in the human gut, more preferably in the gut of healthy human subjects.

Examples of bacterial probiotic strains or species that may be used in the present invention include, but are not limited to *Lactobacillus, Lactococcus, Bifidobacterium, Veillonella, Desemzia, Christensenella, Allobaculum, Coprococcus, Collinsella, Citrobacter, Turicibacter, Sutterella, Subdoligranulum, Streptococcus, Sporobacter, Sporacetigenium, Ruminococcus, Roseburia, Proteus, Propionobacterium, Leuconostoc, Weissella, Pediococcus, Streptococcus, Prevotella, Parabacteroides, Papillibacter, Oscillospira, Melissococcus, Dorea, Dialister, Clostridium, Cedecea, Catenibacterium, Butyrivibrio, Buttiauxella, Bulleidia, Bilophila, Bacteroides, Anaerovorax, Anaerostopes, Anaerofilum, Enterobacteriaceae, Fermicutes, Atopobium, Alistipes, Acinetobacter, Slackie, Shigella, Shewanella, Serratia, Mahella, Lachnospira, Klebsiella, Idiomarina, Fusobacterium, Faecalibacterium, Eubacterium, Enterococcus, Enterobacter, Eggerthella.*

In one particular embodiment, said bacterial probiotic strains or species are selected from the list comprising *Bifidobacterium* and *Lactobacillus*. In one embodiment, *Bifidobacterium* probiotic strains or species are preferably selected from the group comprising *Bifidobacterium animalis*, more preferably *Bifidobacterium animalis* spp. *lactis*, and *Bifidobacterium lactis*. In one embodiment, *Lactobacillus* probiotic strains or species are preferably selected from the group comprising *Lactobacillus rhamnosus, Lactobacillus casei* and *Lactobacillus acidophilus*.

Examples of prokaryote strains or species that may be used in the present invention include, but are not limited to Archaea, Firmicutes, Verrucomicrobia, Christensenella, Bacteroidetes (such as, for example, *Allistipes, Bacteroides ovatus, Bacteroides splachnicus, Bacteroides stercoris, Parabacteroides, Prevotella ruminicola, Porphyromondaceae,* and related genus), Proteobacteria, Betaproteobacteria (such as, for example, *Aquabacterium* and *Burkholderia*), Gammaproteobacteria (such as, for example, *Xanthomonadaceae*), Actinobacteria (such as, for example, *Actinomycetaceae* and *Atopobium*), Fusobacteria, Methanobacteria, Spirochaetes, Fibrobacteres, Deferribacteres, *Deinococcus, Thermus,* Cyanobacteria, Methanobrevibacteria, *Peptostreptococcus, Ruminococcus, Coprococcus, Subdolingranulum, Dorea, Bulleidia, Anaerofustis, Gemella, Roseburia, Dialister, Anaerotruncus, Staphylococcus,*

*Micrococcus*, Propionobacteria, Enterobacteriaceae, *Faecalibacterium, Bacteroides, Parabacteroides, Prevotella, Eubacterium*, Bacilli (such as, for example, *Lactobacillus salivarius* and related species, *Aerococcus, Granulicatella, Streptococcus bovis* and related genus and *Streptococcus intermedius* and related genus), *Clostridium* (such as, for example, *Eubacterium hallii, Eubacterium limosum* and related genus) and *Butyrivibrio*.

Examples of fungal probiotic strains or species, preferably yeast probiotic strains or species that may be used in the present invention include, but are not limited *Ascomycetes, Zygomycetes* and *Deuteromycetes*, preferably from the groups *Aspergillus, Torulopsis, Zygosaccharomyces, Hansenula, Candida, Saccharomyces, Clavispora, Bretanomyces, Pichia, Amylomyces, Zygosaccharomyces, Endomycess, Hyphopichia, Zygosaccharomyces, Kluyveromyces, Mucor, Rhizopus, Yarrowia, Endomyces, Debaryomyces*, and/or *Penicillium*.

In one embodiment of the invention, the composition, the pharmaceutical composition, the cosmetic composition or the medicament does not comprise the bacterial strains *Lactobacillus-Enterococcus, Bacteroides* and/or *Atopobium*.

In one embodiment of the invention, the only one microbial strain or species, preferably bacterial strain or species, comprised in the composition, pharmaceutical composition, cosmetic composition or medicament is *Akkermansia muciniphila*.

In one embodiment of the invention, the composition, pharmaceutical composition, cosmetic composition or medicament consists of pasteurized *Akkermansia muciniphila*.

In another embodiment of the invention, the composition, pharmaceutical composition, cosmetic composition or medicament consists essentially of pasteurized *Akkermansia muciniphila*, wherein "consisting essentially of" herein means that *Akkermansia muciniphila* is the only microbial strain or species, preferably the only bacterial strain or species comprised in the composition, pharmaceutical composition, cosmetic composition or medicament.

In one embodiment of the invention, pasteurized *Akkermansia muciniphila* or a fragment thereof activates or inhibits the growth and/or biological activity of other bacterial strain(s) or species of the gut microbiota.

In one embodiment of the invention, the composition, the pharmaceutical composition, the cosmetic composition or the medicament further comprises a prebiotic.

Examples of prebiotics that may be used in the present invention include, but are not limited to, inulin and inulin-type fructans, oligofructose, beta-glucans, xylose, arabinose, arabinoxylan, ribose, galactose, rhamnose, cellobiose, fructose, lactose, salicin, sucrose, glucose, esculin, tween 80, trehalose, maltose, mannose, mellibiose, mucus or mucins, raffinose, fructooligosaccharides, galacto-oligosaccharides, amino acids, alcohols, fermentable carbohydrates and any combinations thereof.

Other non-limiting examples of prebiotics include water-soluble cellulose derivatives, water-insoluble cellulose derivatives, unprocessed oatmeal, metamucil, all-bran, and any combinations thereof.

Examples of water-soluble cellulose derivatives include, but are not limited to, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose.

Pasteurized *Akkermansia muciniphila* or a fragment thereof or the composition, pharmaceutical composition, cosmetic composition or medicament of the invention may be administered by several routes of administration. Examples of adapted routes of administration include, but are not limited to, oral administration, rectal administration, administration via esophagogastroduodenoscopy, administration via colonoscopy, administration using a nasogastric or orogastric tube and the like.

According to an embodiment, pasteurized *Akkermansia muciniphila* or a fragment thereof or the composition, pharmaceutical composition, cosmetic composition or medicament of the invention is in a form adapted to oral administration. According to a first embodiment, the form adapted to oral administration is a solid form selected from the group comprising tablets, pills, capsules, soft gelatin capsules, sugarcoated pills, orodispersing tablets, effervescent tablets or other solids. According to a second embodiment, the form adapted to oral administration is a liquid form, such as, for example, a drinkable solution, liposomal forms and the like.

In one embodiment, the composition, pharmaceutical composition, cosmetic composition or medicament of the invention further comprises excipients, diluent and/or carriers selected with regard to the intended route of administration. Examples of excipients, diluent and/or carriers include, but are not limited to, water, phosphate buffer saline, anaerobic phosphate buffer saline, sodium bicarbonate, juice, milk, yogurt, infant formula, dairy product, coloring agents, such as, for example, titane dioxide (E171), iron dioxide (E172) and brilliant black BN (E151); flavoring agents; thickeners, such as, for example, glycerol monostearate; sweeteners; coating agents, such as, for example, refined colza oil, soya oil, peanut oil, soya lecithin or fish gelatin; diluting agents, such as, for example, lactose, monohydrated lactose or starch; binding agents, such as, for example, povidone, pregelatinized starch, gums, saccharose, polyethylene glycol (PEG) 4000 or PEG 6000; disintegrating agents, such as, for example, microcrystalline cellulose or sodium carboxymethyl starch, such as, for example, sodium carboxymethyl starch type A; lubricant agents, such as, for example, magnesium stearate; flow agent, such as, for example, colloidal anhydrous silica, etc . . . .

In one embodiment of the invention, the composition, pharmaceutical composition, cosmetic composition or medicament is in the form of a nutritional composition, i.e. comprises liquid or solid food, feed or drinking water. In one embodiment of the invention, the composition, pharmaceutical composition, cosmetic composition or medicament is a food product, such as, for example, dairy products, dairy drinks, yogurt, fruit or vegetable juice or concentrate thereof, powders, malt or soy or cereal based beverages, breakfast cereal such as muesli flakes, fruit and vegetable juice powders, cereal and/or chocolate bars, confectionary, spreads, flours, milk, smoothies, confectionary, milk product, milk powder, reconstituted milk, cultured milk, yoghurt, drinking yoghurt, set yoghurt, drink, dairy drink, milk drink, chocolate, gels, ice creams, cereals, reconstituted fruit products, snack bars, food bars, muesli bars, spreads, sauces, dips, dairy products including yoghurts and cheeses, drinks including dairy and non-dairy based drinks, sports supplements including dairy and non-dairy based sports supplements.

In one embodiment of the invention, the composition, pharmaceutical composition, cosmetic composition or medicament is in the form of a food additive, drink additive, dietary supplement, nutritional product, medical food or nutraceutical composition.

It is known that obesity and related disorders are associated with an increased gut permeability and with impaired mucus production, epithelium barrier, immune system and/ or antibacterial compounds production by the subject; and the Applicant suggests that the administration of pasteurized *Akkermansia muciniphila* may restore these parameters. Therefore, the present invention also relates to pasteurized *Akkermansia muciniphila* or a fragment thereof for decreasing gut permeability and/or for restoring impaired mucus production and/or for restoring epithelium barrier and/or for restoring immune system and/or for restoring the production of antibacterial compounds. Another object of the invention is a method for decreasing gut permeability and/or for restoring impaired mucus production and/or for restoring epithelium barrier and/or for restoring immune system and/or for restoring the production of antibacterial compounds in a subject in need thereof, comprising administering an effective or cosmetically effective amount of pasteurized *Akkermansia muciniphila* or a fragment thereof to a subject in need thereof.

Therefore, the present invention also relates to pasteurized *Akkermansia muciniphila* or a fragment thereof for controlling gut barrier function, and to a method for controlling gut barrier function comprising administering an effective or cosmetically effective amount of pasteurized *Akkermansia muciniphila* or a fragment thereof to a subject in need thereof. In one embodiment, pasteurized *Akkermansia muciniphila* or a fragment thereof regulates mucus layer thickness (which may be decreased in obesity or other metabolic disorders). In another embodiment, the administration of pasteurized *Akkermansia muciniphila* or a fragment thereof induces the production of colon antimicrobial peptides, such as, for example, RegIIIgamma. In another embodiment, the administration of pasteurized *Akkermansia muciniphila* or a fragment thereof induces the production of compounds of the endocannabinoids family, such as, for example, acylglycerols selected from the group comprising 2-oleoylglycerol, 2-palmitoylglycerol and 2-arachidonoylglycerol. In another embodiment, the administration of pasteurized *Akkermansia muciniphila* or a fragment thereof regulates mucus turnover.

Another object of the invention concerns pasteurized *Akkermansia muciniphila* or a fragment thereof for use in treating metabolic dysfunction associated with or caused by a metabolic disorder. Still another object of the invention is thus a method for treating metabolic dysfunction associated with or caused by a metabolic disorder in a subject in need thereof, comprising administering an effective amount or a cosmetically effective amount of pasteurized *Akkermansia muciniphila* or a fragment thereof to a subject in need thereof.

The Applicant also showed that the administration of pasteurized *Akkermansia muciniphila* controls fat storage and adipose tissue metabolism. Therefore, another object of the invention concerns pasteurized *Akkermansia muciniphila* or a fragment thereof for use in controlling fat storage and adipose tissue metabolism. Another object of the invention is also a method for controlling fat storage and adipose tissue metabolism comprising administering an effective amount or a cosmetically effective amount of pasteurized *Akkermansia muciniphila* or a fragment thereof to a subject in need thereof. In one embodiment, said control does not involve any change in food intake. In one embodiment of the invention, administration of pasteurized *Akkermansia muciniphila* or a fragment thereof abolishes metabolic endotoxemia. In another embodiment, administration of pasteurized *Akkermansia muciniphila* or a fragment thereof lowers fat mass. In another embodiment, administration of pasteurized *Akkermansia muciniphila* or a fragment thereof increases mRNA expression of markers of adipocyte differentiation and lipid oxidation, preferably without affecting lipogenesis.

The present invention also relates to pasteurized *Akkermansia muciniphila* or a fragment thereof for use in the regulation of adipose tissue metabolism and glucose homeostasis; and to a method for regulating adipose tissue metabolism and glucose homeostasis comprising administering an effective amount or a cosmetically effective amount of pasteurized *Akkermansia muciniphila* or a fragment thereof to a subject in need thereof. In one embodiment of the invention, the administration of pasteurized *Akkermansia muciniphila* or a fragment thereof reverses diet-induced fasting hyperglycemia. In another embodiment, the administration of pasteurized *Akkermansia muciniphila* or a fragment thereof induces a reduction of at least 10%, preferably of at least 30%, more preferably of at least 40% of hepatic glucose-6-phosphatase expression. In another embodiment, the administration of pasteurized *Akkermansia muciniphila* or a fragment thereof induces a reduction of the insulin-resistance index. In one embodiment, said reduction of the insulin-resistance index is of at least 5%, preferably of at least 10%, more preferably of at least 15%, 20%, 25%, 30%, 35%, 40%, 45% or 50%.

The Applicant showed that the administration of pasteurized *Akkermansia muciniphila* decreases glucose intolerance and insulin resistance in high-fat diet fed mice. Therefore, the present invention also relates to pasteurized *Akkermansia muciniphila* or a fragment thereof for decreasing glucose intolerance and/or insulin resistance; and to a method for decreasing glucose intolerance and/or insulin resistance comprising administering an effective amount or a cosmetically effective amount of pasteurized *Akkermansia muciniphila* or a fragment thereof to a subject in need thereof.

The present invention also relates to pasteurized *Akkermansia muciniphila* or a fragment thereof for treating inflammation, preferably low grade inflammation, associated with or caused by metabolic disorders; and to a method for treating inflammation related to metabolic disorders comprising administering an effective amount or a cosmetically effective amount of pasteurized *Akkermansia muciniphila* or a fragment thereof to a subject in need thereof.

The Applicant showed that the administration of pasteurized *Akkermansia muciniphila* decreases plasma triglycerides levels in treated mice. Therefore, the present invention also relates to pasteurized *Akkermansia muciniphila* or a fragment thereof for decreasing plasma triglycerides levels; and to a method for decreasing plasma triglycerides levels comprising administering an effective amount or a cosmetically effective amount of pasteurized *Akkermansia muciniphila* or a fragment thereof to a subject in need thereof.

The present invention also relates to pasteurized *Akkermansia muciniphila* or a fragment thereof for decreasing plasma cholesterol; and to a method for decreasing plasma cholesterol comprising administering an effective amount or a cosmetically effective amount of pasteurized *Akkermansia muciniphila* or a fragment thereof to a subject in need thereof.

In one embodiment of the invention, the administration of pasteurized *Akkermansia muciniphila* or a fragment thereof to a subject has no impact on food intake of said subject.

In one embodiment of the invention, the administration of pasteurized *Akkermansia muciniphila* or a fragment thereof to a subject increases energy expenditure of said subject, preferably without impacting the food intake of said subject.

The present invention thus also relates to a method of increasing energy expenditure of a subject, comprising administering pasteurized *Akkermansia muciniphila* or a fragment thereof, or a composition, pharmaceutical composition, cosmetic composition or medicament of the invention to the subject, preferably in a therapeutically or cosmetically effective amount. Preferably, the method of the invention does not comprise or further comprise modulating the food intake of said subject. In one embodiment of the invention, the method of the invention increases energy expenditure, thereby inducing durable weight loss in the subject, and thereby treating metabolic disorders in said subject, such as, for example, obesity related metabolic disorders.

In one embodiment, the administration of pasteurized *Akkermansia muciniphila* or a fragment thereof to a subject increases satiety in said subject. Consequently, according to this embodiment, the method of the invention increases satiety in a subject, thereby inducing durable weight loss in the subject, and thereby treating metabolic disorders in said subject, such as, for example, obesity related metabolic disorders.

BRIEF DESCRIPTION OF THE DRAWINGS

FIG. 14 is a set of graphs showing the safety assessment of *A. muciniphila* after oral administration in overweight/obese patients (n=5). (A-C) Markers related to inflammation and hematology: (A) C-reactive protein (mg/dl), (B) Total white blood cell count ($10^3$ cells/µL), (C) Prothrombin time (sec). (D-F) Markers related to kidney function: (D) Urea (mg/dl), (E) Creatinine (mg/dl), (F) Glomerular filtration rate (mL/min*1.73 m$^2$). (G-I) Markers related to liver function: (G) Alanine transaminase activity (IU/1), (H) Aspartate transaminase activity (IU/1), (I) γ-glutamyltranspeptidase activity (IU/1). (J-K) Markers related to muscle function: (J) Creatinine kinase activity (IU/1), (K) Lactate dehydrogenase activity (IU/1).

EXAMPLES

Figure 1:
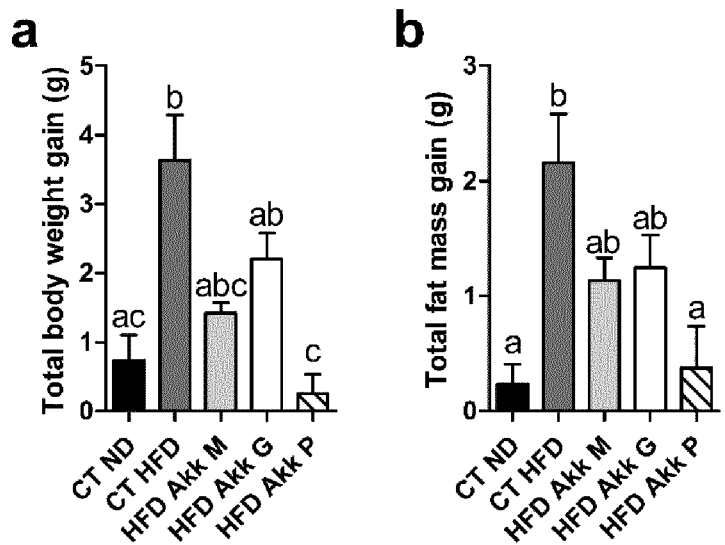
FIG. 1 is a set of histograms showing that *Akkermansia muciniphila* grown on a mucus-based medium or on a non-mucus-based growth medium counteracts the increase in body weight gain and fat mass gain in mice fed a high-fat diet. Furthermore, effects of pasteurized *A. muciniphila* on body weight gain and fat mass gain are stronger than with the live bacterium. (a) Total body weight gain (g) in mice fed a control diet (CT ND), a high-fat diet (CT HFD) and treated daily by oral gavage with sterile anaerobic PBS containing glycerol or mice fed a high-fat diet and treated daily by oral gavage with live *A. muciniphila* grown on a mucus-based medium (HFD Akk M), a non-mucus-based medium (HFD Akk G), or *A. muciniphila* grown on a mucus-based medium and pasteurized (HFD Akk P) for 4 weeks (n=8-10). ($2.10^8$ bacterial cells suspended in 150 μt of sterile anaerobic PBS). (b) Total fat mass gain (g) measured by time-domain nuclear magnetic resonance (n=8-10). Data are shown as mean±SEM. Data with different superscript letters are significantly different (P<0.05), according to one-way ANOVA analysis followed by Tukey post-hoc test.

The present invention is further illustrated by the following examples.

We previously showed that daily administration of *Akkermansia muciniphila* to mice fed a high-fat diet can impede the development of obesity (WO 2014/076246).

With the perspective of transferring these results to clinical settings, we decided to assess whether *A. muciniphila* would retain its effects when cultured on a non-mucus-based medium suited for human trials. Moreover, our previous results indicated that autoclaving *A. muciniphila* abolished its effect on diet-induced obesity. We therefore sought to investigate the consequences of another inactivation method (i.e. pasteurization) on *A. muciniphila*-mediated effects.

Materials and Methods

Mice

First experiment: a set of 10-week-old C57BL/6J mice (50 mice, n=10/group) (Charles River, L'Arbresle, France) were housed in a controlled environment (12 h daylight cycle, lights off at 6 pm) in groups of two mice per cage, with free access to food and water. Mice were fed a control diet (ND) (AIN93Mi, Research diet, New Brunswick, N.J., USA) or a high-fat diet (HFD) (60% fat and 20% carbohydrates (kcal/100 g) D12492i, Research diet, New Brunswick, N.J., USA).

Mice were treated daily with an oral administration of *Akkermansia muciniphila* grown on a mucin-based medium (HFD Akk M) or a non-mucus-based medium (HFD Akk G) by oral gavage at the dose of $2.10^8$ cfu/0.15 mL suspended in sterile anaerobic phosphate buffer saline (PBS). Additionally, one group of mice was treated daily with an oral administration of *Akkermansia muciniphila* grown on a non-mucus-based medium and inactivated by pasteurization (HFD Akk P). Control groups were treated with an oral gavage of an equivalent volume of sterile anaerobic PBS (CT ND and CT HFD) containing a similar end concentration of glycerol (2.5% vol/vol). Treatment was continued for 4 weeks.

For the HFD Akk M group, *A. muciniphila* MucT (ATTC BAA-835) was grown anaerobically in a mucin-based basal medium as previously described (Derrien et al., 2004. *Int. J. Syst. Evol. Microbiol.* 54:1469-1476). Cultures were then washed and suspended in anaerobic PBS, including 25% (v/v) glycerol, to an end concentration of $1.10^{10}$ cfu/mL.

For the HFD Akk G group, *A. muciniphila* MucT (ATTC BAA-835) was grown anaerobically in non-mucus-based medium. Cultures were then washed and suspended in anaerobic PBS, including 25% (v/v) glycerol, to an end concentration of $1.10^{10}$ cfu/mL.

For the HFD Akk P group, *A. muciniphila* MucT (ATTC BAA-835) was grown anaerobically in non-mucus-based medium Cultures were then washed and suspended in anaerobic PBS, including 25% (v/v) glycerol, to an end concentration of $1.10^{10}$ cfu/mL. Vials were then pasteurized by exposure to a temperature of 70° C. for 30 minutes in a water bath.

Body weight, food and water intake were recorded once a week. Body composition was assessed by using 7.5 MHz time domain-nuclear magnetic resonance (TD-NMR) (LF50 minispec, Bruker, Rheinstetten, Germany).

Second experiment: a set of 10-week-old C57BL/6J mice (40 mice, n=10/group) (Charles River, L'Arbresle, France) were housed in a controlled environment (12 h daylight cycle, lights off at 6 pm) in groups of two mice per cage, with free access to food and water. Mice were fed a control diet (ND) (AIN93Mi; Research diet, New Brunswick, N.J., USA) or a high-fat diet (HFD) (60% fat and 20% carbohydrates (kcal/100 g), Research diet D12492i, New Brunswick, N.J., USA). Mice were treated daily with an oral administration of *Akkermansia muciniphila* grown on a non-mucus-based medium and either live or pasteurized (HFD Akk G and HFD Akk P) by oral gavage at the dose of $2.10^8$ cfu/0.15 mL suspended in sterile anaerobic phosphate buffer saline. Control groups were treated with an oral gavage of an equivalent volume of sterile anaerobic phosphate buffer saline (CT ND and CT HFD). Treatment was continued for 5 weeks.

For the HFD Akk G group, *A. muciniphila* MucT (ATTC BAA-835) was grown anaerobically in non-mucus-based medium. Cultures were then washed and suspended in anaerobic PBS, including 25% (v/v) glycerol, to an end concentration of $1.10^{10}$ cfu/mL.

For the HFD Akk P group, *A. muciniphila* MucT (ATTC BAA-835) was grown anaerobically in non-mucus-based medium. Cultures were then washed and suspended in anaerobic PBS, including 25% (v/v) glycerol, to an end concentration of $1.10^{10}$ cfu/mL. Vials were then pasteurized by exposure to a temperature of 70° C. for 30 minutes in a water bath.

Body weight, food and water intake were recorded once a week. Body composition was assessed by using 7.5 MHz time domain-nuclear magnetic resonance (TD-NMR) (LF50 minispec, Bruker, Rheinstetten, Germany).

Fresh urinary samples were collected during the final week of treatment and directly stored at −80° C. before analysis. Fecal energy content was measured on fecal samples harvested after a 24 h period during the final week of treatment by the use of a bomb calorimeter (Mouse Clinical Institute, 67404 Illkirch, France).

Third experiment: a set of 10-week-old C57BL/6J mice (40 mice, n=10/group) (Charles River, L'Arbresle, France) were housed in a controlled environment (12 h daylight cycle, lights off at 6 pm) in groups of two mice per cage, with free access to food and water. Mice were fed a control diet (CT ND) (AIN93Mi; Research diet, New Brunswick, N.J., USA) or a high-fat diet (CT HFD) (60% fat and 20% carbohydrates (kcal/100 g), Research diet D12492i, New Brunswick, N.J., USA). Mice were treated daily with an oral administration of *Akkermansia muciniphila* grown on a non-mucus-based medium and either live or pasteurized (HFD Akk G and HFD Akk P) by oral gavage at the dose of $2.10^8$ CFU/0.15 mL suspended in sterile anaerobic phosphate buffer saline. Control groups were treated with an oral gavage of an equivalent volume of sterile anaerobic phosphate buffer saline (CT ND and CT HFD). Treatment was continued for 5 weeks.

All mouse experiments were approved by and performed in accordance with the guidelines of the local ethics committee. Housing conditions were specified by the Belgian Law of May 29, 2013, regarding the protection of laboratory animals (agreement number LA1230314).

Oral Glucose Tolerance Test 6 h-fasted mice were treated with an oral gavage glucose load (2 g glucose per kg body weight). Blood glucose levels were measured before oral glucose load and 15, 30, 60, 90 and 120 minutes after oral glucose load. Blood glucose was determined with a glucose meter (Accu Check, Aviva, Roche) on blood samples collected from the tip of the tail vein.

Insulin Resistance Index

Plasma insulin concentration was determined in 5 μL of plasma using an ELISA kit (Mercodia) according to the manufacturer's instructions. Insulin resistance index was determined by multiplying the area under the curve of both blood glucose (−30 to 120 minutes) and plasma insulin (−30 and 15 minutes) obtained following the oral glucose tolerance test.

Western-Blot

To analyze the insulin signaling pathway in the third experiment, mice were allocated in either a saline-injected subgroup or an insulin-injected subgroup so that both subgroups were matched in terms of body weight and fat mass. They then received 1 mU/g insulin (Actrapid; Novo Nordisk A/S, Denmark) under anaesthesia (isoflurane, Forene, Abbott, Queenborough, Kent, England), or an equal volume of saline solution into the portal vein. Three minutes after injection, mice were killed and liver was rapidly harvested.

For detection of proteins of the insulin pathway, tissues were homogenized in ERK buffer (Triton X-100 0.1%, HEPES 50 mM, NaCl 5 M, Glycerol 10%, $MgCl_2$ 1.5 mM and DTT 1 mM) supplemented with a cocktail of protease inhibitors and phosphatase inhibitors. Equal amounts of proteins were separated by SDS-PAGE and transferred to nitrocellulose membranes. Membranes were incubated overnight at 4° C. with antibodies diluted in Tris-buffered saline Tween-20 containing 1% non-fat dry milk: p-IRb (1:1,000; sc-25103, Santa Cruz, Calif., USA), p-AktThr308 (1:1.000; #2965L, Cell Signaling, Danvers, Mass., USA) and p-AktSer473 (1:1.000; #4060L, Cell Signaling). Quantification of phosphoproteins was performed on 5 animals with insulin injection and 5 animals with saline injection per group. The loading control was β-actin (1:10000; ab6276).

Tissue Sampling

The animals have been anesthetized with isoflurane (Forene®, Abbott, Queenborough, Kent, England) and blood was sampled from the portal and cava veins. Mice were then killed by cervical dislocation before proceeding to tissue sampling. Adipose depots (epididymal, subcutaneous and mesenteric) were precisely dissected and weighed; the addition of the weights of all three adipose tissue depots corresponds to the adiposity index. The intestinal segments (ileum, cecum and colon), cecal content and adipose tissue depots were immersed in liquid nitrogen, and stored at −80° C., for further analysis.

Histological Analyses

Adipose tissues were fixed in 4% paraformaldehyde for 24 hours at room temperature. Then the samples were immersed in ethanol 100% for 24 hours prior to processing for paraffin embedding. Tissue samples, paraffin sections of 5 μm, were stained with haematoxylin and eosin. Images were obtained using the SCN400 slide scanner (Leica Biosystems, Wetzlar, Germany). 5 high-magnification fields were selected at random for each mouse and adipocyte diameter was determined using ImageJ (Version 1.50a, National Institutes of Health, Bethesda, Md., USA).

RNA Preparation and Real-Time qPCR Analysis

Total RNA was prepared from tissues using TriPure reagent (Roche). Quantification and integrity analysis of total RNA was performed by running 1 μL of each sample on an Agilent 2100 Bioanalyzer (Agilent RNA 6000 Nano Kit, Agilent). cDNA was prepared by reverse transcription of 1 μg total RNA using a Reverse Transcription System kit (Promega, Leiden, The Netherlands). Real-time PCRs were performed with the Biorad CFX real-time PCR system and software (Biorad, Hercules, United States) using Mesa Fast qPCR (Eurogentec, Seraing, Belgium) for detection according to the manufacturer's instructions. RPL19 was chosen as the housekeeping gene. All samples were run in duplicate in a single 96-well reaction plate, and data were analyzed according to the $2^{\Delta\Delta CT}$ method. The identity and purity of the amplified product was checked through analysis of the melting curve carried out at the end of amplification. Primer sequences for the targeted mouse genes are presented in Table 1 below.

TABLE 1

Primer sequences for the targeted mouse genes.

| Primers | | Sequence |
|---|---|---|
| RPL-19 | Forward | GAAGGTCAAAGGGAATGTGTTCA (SEQ ID NO: 1) |
| | Reverse | CCTTGTCTGCCTTCAGCTTGT (SEQ ID NO: 2) |
| Ocln | Forward | ATGTCCGGCCGATGCTCTC (SEQ ID NO: 3) |
| | Reverse | TTTGGCTGCTCTTGGGTCTGTAT (SEQ ID NO: 4) |
| Cldn3 | Forward | TCATCGGCAGCAGCATCATCAC (SEQ ID NO: 5) |
| | Reverse | ACGATGGTGATCTTGGCCTTGG (SEQ ID NO: 6) |
| Lyz1 | Forward | GCCAAGGTCTACAATCGTTGTGAGTTG (SEQ ID NO: 7) |
| | Reverse | CAGTCAGCCAGCTTGACACCACG (SEQ ID NO: 8) |

Measurement of Plasma Triglycerides

Plasma samples were assayed for triglycerides by measuring the glycerol resulting from hydrolysis of triglycerides, using a commercial kit (DiaSys, Condom, France).

Measurement of Plasma Leptin

Plasma samples were assayed for leptin through the use of a multiplex immunoassay kit (Merck Millipore, Brussels, Belgium) and measured using Luminex technology (Bioplex, Bio-Rad, Belgium) following the manufacturer's instructions.

Measurement of Plasma Cholesterol (Fast Protein Liquid Chromatography, FLPC)

Quantification of plasma lipoproteins was performed using fast protein liquid chromatography (FPLC, AKTA purifier 10, GE Healthcare, Chicago, Ill., USA). 50 μL of individual plasma was injected and lipoproteins were separated on Superose™ 6 10/300 GL column (GE Healthcare, Chicago, Ill., USA) with NaCl 0.15 Mat pH 7.4 as mobile phase at a 1 mL/min flow rate. The effluent was collected into fractions of 0.3 mL then cholesterol and TG content in each fraction were determined as described above. Quantification of cholesterol in lipoprotein classes (VLDL, LDL, and HDL) was performed by measuring the percentage peak area and by multiplying each percentage to the total amount of cholesterol. Plasma total cholesterol was measured with commercial kits (CHOD-PAP; BIOLABO SA, Maizy, France).

Measurement of Fecal Energy

Fecal energy content was measured on fecal samples harvested after a 24 h-period during the final week of treatment by the use of a bomb calorimeter (Mouse Clinical Institute, Illkirch, France).

Urinary Metabolomics Analyses

Mouse urine samples were prepared and measured on a spectrometer (Bruker) operating at 600.22 MHz 1H frequency according to previously published protocol (Dona A C, 2014); the $^1$H NMR spectra were then processed and analyzed as described previously (Dumas et al., 2006. Proc. Natl. Acad. Sci. USA. 103(33):12511-6).

Quantification of Plasma Lipopolysaccharide

Portal vein blood LPS concentration was measured using an Endosafe-Multi-Cartridge System (Charles River Laboratories) based on the Limulus amaebocyte lysate (LAL) kinetic chromogenic methodology that measures color intensity directly related to the endotoxin concentration in a sample. Plasmas were diluted 1/10 with endotoxin-free buffer to minimize interferences in the reaction (inhibition or enhancement) and heated 15 minutes at 70° C. Each sample was diluted 1/100, 1/150, 1/200 or 1/400 with endotoxin-free LAL reagent water (Charles River Laboratories) and treated in duplicate, and two spikes for each sample were included in the determination. All samples have been validated for the recovery and the coefficient variation. The lower limit of detection was 0.005 EU/mL.

Determination of the Pasteurization Temperature and Time Range

Vials containing live bacteria were immersed in a water bath set to 50, 60, 70, 80 or 90° C. for 15 seconds (0.25 minutes), 2 minutes, 5 minutes, 15 minutes and 30 minutes. Inactivation of A. muciniphila was assessed by plating 50 μL of undiluted vial content on Brain-Heart Infusion (BHI)-Agar medium supplemented with 5% mucus and looking for the presence of colony-forming units (cfu) after 7 days of incubation at 37° C. in an anaerobic container. Content of an autoclaved vial was used as a negative control, and content from a vial non immersed in a water bath was used as a positive control. This experiment was performed at two different times.

Mucus-Based Medium

A. muciniphila was grown in mucus-based medium, washed and concentrated as described previously (Everard et al., 2013. Proc. Natl. Acad. Sci. USA. 110:9066-9071). In addition to an untreated batch of cells, one part was subject to a mild heat treatment by a 30-minute incubation at 70° C.

Non-Mucus-Based Medium

A. muciniphila was grown in a non-mucus-based medium consisting of basal anaerobic medium as described previously (Derrien et al., 2004. Int. J. Syst. Evol. Microbiol. 54:1469-1476) containing 16 g/L soy-based pepton, 25 mM glucose and 25 mM N-acetyl-glucosamine and 4 g/L L-threonine. The cells were washed and concentrated as described previously (Everard et al., 2013. Proc. Natl. Acad. Sci. USA. 110:9066-9071). In addition to an untreated batch of cells, one part was subject to a mild heat treatment by a 30-minute incubation at 70° C.

Safety Assessment of Oral Administration of Live and Pasteurized *A. muciniphila* in Overweight or Obese Volunteers Results presented are interim safety reports from twenty overweight and obese patients (Body mass index >25 kg/m$^2$) presenting a metabolic syndrome following the NCEP ATP III definition (any three of the five following criteria: fasting glycaemia >110 mg/dL, blood pressure ≥130/85 mm Hg or antihypertensive treatment, fasting triglyceridemia ≥150 mg/dL, HDL cholesterol <40 mg/dL for males, 50 mg/dL for females, and/or waist circumference >102 cm for males, 88 cm for females). Patients were voluntarily recruited from the Cliniques Universitaires Saint Luc, Brussels, Belgium between December 2015 and May 2016. Subjects were assigned to any of the treatment arms following a randomized block design. The exclusion criteria were: presence of acute or chronic progressive or chronic unstabilized diseases, alcohol consumption (>2 glasses/day), previous bariatric surgery, any surgery in the 3 months prior to the study or planned in the next 6 months, pregnancy or pregnancy planned in the next 6 months, regular physical activity (>30 minutes of sports 3 times a week), consumption of dietary supplements (omega-3 fatty acids, probiotics, prebiotics, plant stanols/sterols) in the month prior the study, inflammatory bowel disease or irritable bowel syndrome, diabetic gastrointestinal autonomic neuropathy (such as gastroparesis or reduced gastrointestinal motility), consumption of more than 30 g of dietary fibers per day, consumption of vegetarian or unusual diet, lactose intolerance or milk protein allergy, gluten intolerance, current treatment with medications influencing parameters of interest (glucose-lowering drugs such as metformin, DPP-4 inhibitors, GLP-1 receptor agonists, acarbose, sulfonylueras, glinides, thiazolidinediones, SGLT2 inhibitors, insulin, lactulose, consumption of antibiotics in the 2 months prior the study, glucocorticoids, immunosuppressive agents, statins, fibrates, orlistat, cholestyramine, or ezetimibe), and baseline glycated hemoglobin (HbA1c) >7.5%. The Commission d'Ethique Biomédicale Hospitalo-facultaire from the Université catholique de Louvain (Brussels, Belgium) provided ethical approval for this study and written informed consent was obtained from each participant. The trial was registered at clinicaltrials.gov as NCT02637115.

Subjects were assigned to receive either a daily dose of placebo (an equivalent volume of sterile PBS containing glycerol), $10^{10}$ CFU live *A. muciniphila* (Akk S—$10^{10}$), $10^9$ CFU live *A. muciniphila* (Akk S—$10^9$), or $10^{10}$ CFU pasteurized *A. muciniphila* (Akk P—$10^{10}$) (placebo and bacteria were produced at a food-grade level according to good manufacturing practices) for 3 months. Blood samples were collected at the beginning of the treatment and a portion was directly sent to the hospital laboratory to measure relevant clinical parameters. Different tubes were used based on the clinical parameter: EDTA-coated tubes for white blood cell count, Sodium fluoride-coated tubes for fasting glycemia, citrate-coated tubes for clotting assays, and lithium-heparin-coated tubes for urea and enzymatic activities. After 2 weeks of treatment, patients came back to the hospital for a safety visit, where blood samples were collected to allow comparison of clinical parameters to baseline values.

The patients and the physicians were blinded to the treatment. For FIG. 14 and Tables 3-5, the number of subjects per group is: Placebo: 5, Akk S—$10^{10}$: 5, Akk S—$10^9$: 5, Akk P—$10^{10}$: 5.

Statistical Analysis

Data are expressed as means±SEM. Differences between two groups were assessed using the unpaired two-tailed Student's t-test. Data sets involving more than two groups were assessed by ANOVA followed by Tukey post-hoc tests. Data with different superscript letters are significantly different with $P<0.05$, according to the post-hoc ANOVA statistical analysis. Data were analyzed using GraphPad Prism version 5.00 for windows (GraphPad Software, San Diego, Calif., USA). Results were considered statistically significant when $P<0.05$.

A two-way ANOVA analysis with a Bonferonni post-test on repeated measurements was performed for the evolution of glycemia during the OGTT, for the reparation cholesterol in specific lipoproteins and for western-blot analyses.

Human data are expressed as the mean±SD. Differences between groups were assessed using Kruskal-Wallis test. Differences between values observed at baseline and at the time of the safety visit were assessed using a Wilcoxon matched-pairs signed rank test. Data were analyzed using GraphPad Prism version 7.00 for Windows (GraphPad Software, San Diego, Calif., USA). The results were considered statistically significant when $p<0.05$.

Results

In Vitro Experiments

In order to optimize the pasteurization protocol, we first incubated vials containing *A. muciniphila* in water baths set to a range of temperature for different times. Pasteurization was considered effective when no bacteria could be observed after plating the treated vial contents on a rich medium (Table 2).

TABLE 2

Combinations of temperatures and exposure times tested for pasteurization.

| | | Temperature (° C.) | | | | |
|---|---|---|---|---|---|---|
| | | 50 | 60 | 70 | 80 | 90 |
| Exposure (minutes) | 0.25 | Live | Live | Live | Live | Live |
| | 2 | Live | Live | Live | Inactivated | Inactivated |
| | 5 | Live | Live | Borderline | Inactivated | Inactivated |
| | 15 | Live | Borderline | Borderline | Inactivated | Inactivated |
| | 30 | Borderline | Inactivated | Inactivated | Inactivated | Inactivated |

"Live" corresponds to plates where cfu were obtained in high numbers.
"Borderline" corresponds to plates where between 1 and 3 cfu were observed.
"Inactivated" corresponds to plates where no cfu could be observed.

For the further experiments, we have selected a pasteurization of 30 minutes at 70° C. In addition to the viability, the effect of pasteurization has been tested on the activity of two *A. muciniphila* fucosidases and 2 sulfatases (encoded by the genes Amuc_0010, Amuch_0146 and Amuc_0121 and Amuc_1074; van Passel et al., 2011. *PLoS One.* 6(3):

e16876). These enzymes are relevant for the degradation of mucin. For this purpose, their genes were overexpressed in *Escherichia coli* as described with a C-terminal His-tag (Tailford et al., 2015. *Nat. Commun.* 6:7624) and the purified proteins were used for the analysis. The enzyme activities were determined before and after 30 minutes at 70° C. and this treatment completely resulted in an over 20-fold inactivation of the enzymatic activities.

In Vivo Experiments

In a first set of experiments, mice fed a high-fat diet were treated daily with an oral gavage of live *A. muciniphila* grown either on a mucus-based or a non-mucus-based medium. Another group of mice was treated with an oral gavage of *A. muciniphila* grown on a non-mucus-based medium and inactivated by pasteurization (30 minutes at 70° C.). Mice fed standard chow were used as a control group. Treatment was carried on for 4 weeks.

Figure 2:
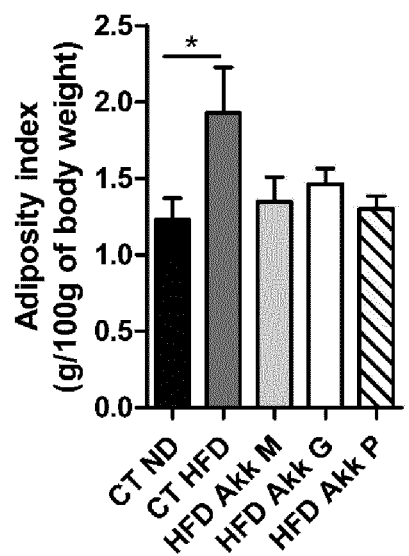
FIG. 2 is a histogram showing normalization of the adiposity index of high-fat diet-fed mice after treatment with *A. muciniphila*. Adiposity index (g) shown as the addition of the weight of the epididymal, subcutaneous and mesenteric adipose depots (n=8-10). Data are shown as mean±SEM. * corresponds to P value <0.05 when two conditions were compared with an unpaired two-tailed Student's t-test.

We observed that live *A. muciniphila* treatment reduced high-fat diet induced body weight and fat mass gain, regardless of the growth medium used (FIG. 1a-b). Surprisingly, pasteurized *A. muciniphila* exerted a stronger effect than the live bacterium, as mice treated with pasteurized cells showed a similar body weight gain and fat mass gain to mice fed a control diet (FIG. 1a-b). Adiposity index, shown as the sum of subcutaneous, visceral and epididymal adipose tissue depots, was significantly increased in mice fed a high-fat diet (FIG. 2). Administration of *A. muciniphila* counteracted this increase, to a similar extent regardless of the growth medium or pasteurization.

Figure 3:
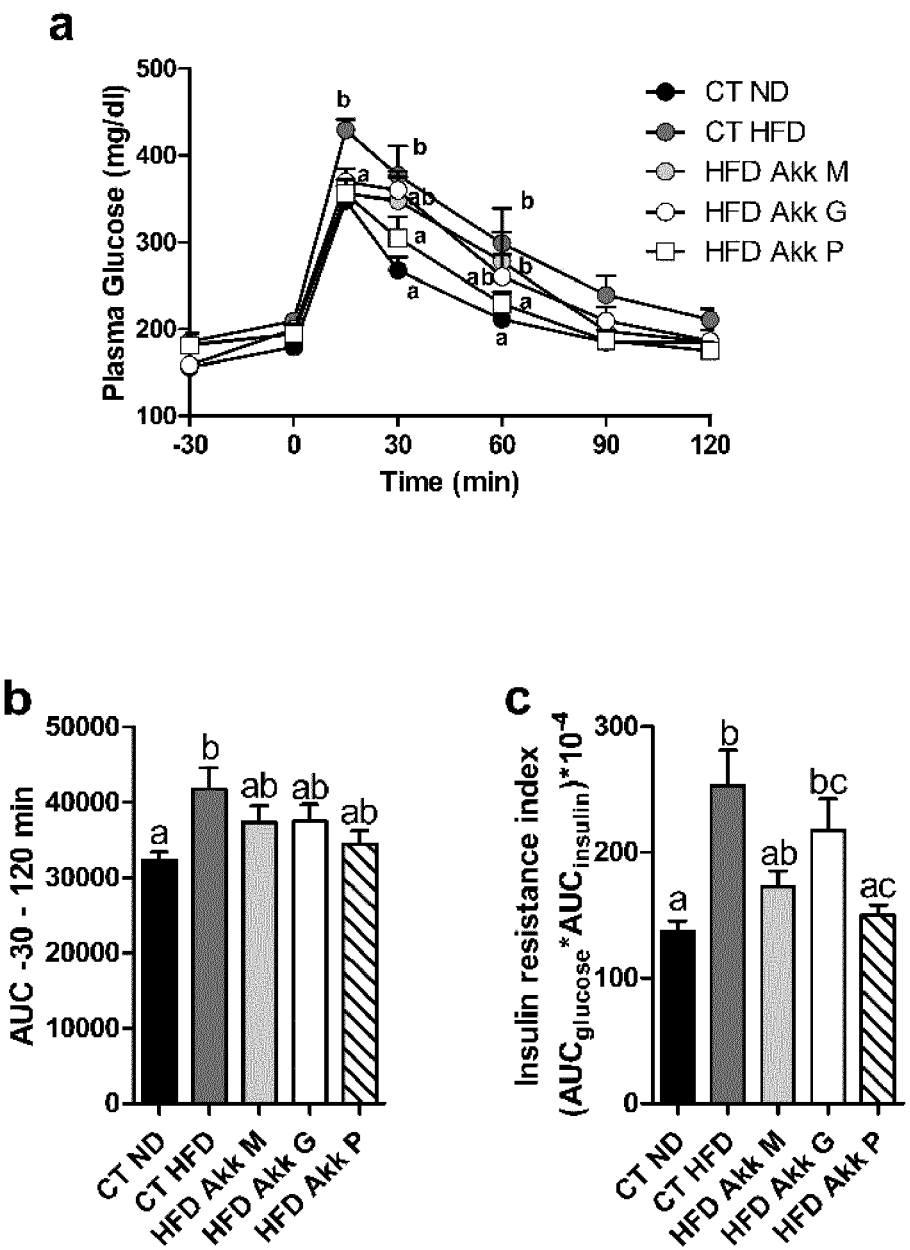
FIG. 3 is a set of graphs showing a diminution of glucose intolerance in mice fed a high-fat diet after administration of pasteurized *A. muciniphila* to a higher extent than administration of live *A. muciniphila* grown either on a mucus-based or non-mucus-based medium. (a) Plasma glucose profile following 2 g/kg glucose oral challenge in freely moving mice (n=8-10). (b) Mean area under the curve (AUC) measured between −30 and 120 min after glucose load (n=8-10). (c) Insulin resistance index, determined by multiplying the AUC of plasma glucose (−30 to 120 min) by the AUC of plasma insulin (−30 to 15 min) (n=8-10). Data are shown as mean±SEM. Data with different superscript letters are significantly different (P<0.05), according to one-way ANOVA analysis followed by Tukey post-hoc test.

We next confirmed our previous results in terms of glucose tolerance. Indeed, a high-fat diet leads to increased glycaemia following an oral glucose tolerance test (OGTT), resulting in a significantly higher area under the curve (AUC) measured between 30 minutes before and 120 minutes after glucose administration (FIG. 3a-b). Administration of *A. muciniphila* mitigated this increase, leading to intermediary AUC values, once again independently of the growth medium and pasteurization.

When taking into account insulinemia of the mice, the insulin resistance index of mice fed a high-fat diet was significantly higher than for control mice (FIG. 3c). Treatment with *A. muciniphila* grown on a mucus-based medium resulted in intermediary insulin resistance (IR) index values between control and untreated high-fat diet-fed mice. However, although the IR index of mice treated with *A. muciniphila* grown on a non-mucus-based medium was 15% lower than for untreated mice fed a high-fat diet, it was still significantly higher than for control mice, while pasteurized *A. muciniphila* completely normalized the IR index of mice fed a high-fat diet (FIG. 3c), thereby showing that pasteurization increases the effects of *Akkermansia muciniphila* on glucose tolerance and insulin resistance.

Figure 4:
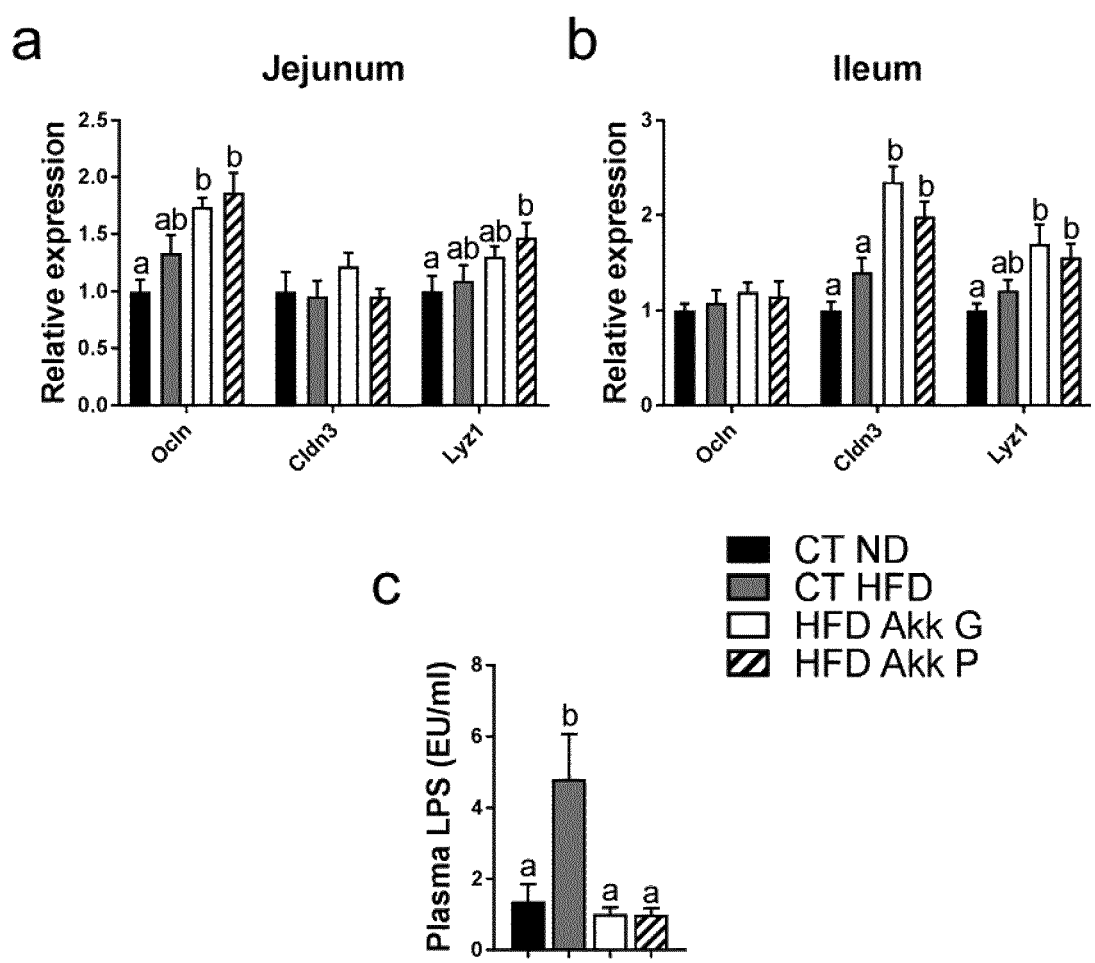
FIG. 4 is a histogram showing modulation of the expression of markers of intestinal integrity and corrects HFD-induced metabolic endotoxemia after administration of *A. muciniphila* grown on a non-mucus-based medium and either live or pasteurized. (a) mRNA expression of Ocln, Cldn3 and Lyz1 in the jejunum (n=7-10), (b) mRNA expression of Ocln, Cldn3 and Lyz1 in the ileum (n=7-10), (c) Plasma Lipopolysaccharide levels (EU/mL) (n=5-9). Data are shown as mean±SEM. Data with different superscript letters are significantly different (P<0.05), according to one-way ANOVA analysis followed by Tukey post-hoc test.

We previously found that treatment with *A. muciniphila* could impact gut barrier function through modulation of antimicrobial peptides production and regulation of mucus layer thickness. To further increase our understanding of the cross-talk between *A. muciniphila* and the intestinal barrier, we measured the expression of two markers of intestinal tight junction proteins, namely Ocln and Cldn3, encoding the proteins Occludin and Claudin 3; as well as Lyz1 encoding the antimicrobial peptide Lysozyme 1. In the jejunum, treatment of HFD-fed mice with live or pasteurized *A. muciniphila* increased the expression of Ocln, while pasteurized *A. muciniphila* specifically increased Lyz1 expression (FIG. 4a). In the ileum, treatment with live and pasteurized *A. muciniphila* increased the expression of Cldn3 and Lyz1 (FIG. 4b). These effects on markers of intestinal integrity resulted in a complete normalization of plasma LPS in treated mice (FIG. 4c), showing that both the live and pasteurized form of *A. muciniphila* can strengthen the intestinal barrier and decrease metabolic endotoxemia.

Figure 5:
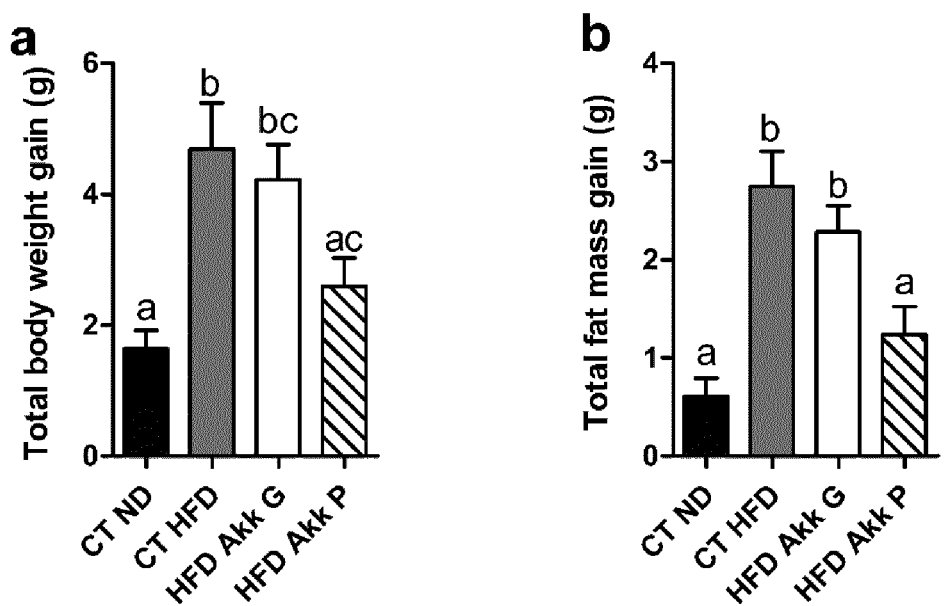
FIG. 5 is a set of histograms showing a reduction of body weight gain and fat mass gain after administration of pasteurized *A. muciniphila* to a higher extent than live *A. muciniphila* grown on a non-mucus-based medium. (a) Total body weight gain (g) in mice fed a control diet (CT ND), a high-fat diet (CT HFD) and treated daily by oral gavage with sterile anaerobic PBS containing glycerol or mice fed a high-fat diet and treated daily by oral gavage with live *A. muciniphila* grown on a non-mucus-based medium (HFD Akk G), or *A. muciniphila* grown on a mucus-based medium and pasteurized (HFD Akk P) (n=16-19) for 5 weeks. ($2.10^8$ bacterial cells suspended in 150 μL of sterile anaerobic PBS). (b) Total fat mass gain (g) measured by time-domain nuclear magnetic resonance (n=16-19). Data are shown as mean±SEM. Data with different superscript letters are significantly different (P<0.05), according to one-way ANOVA analysis followed by Tukey post-hoc test.
Figure 6:
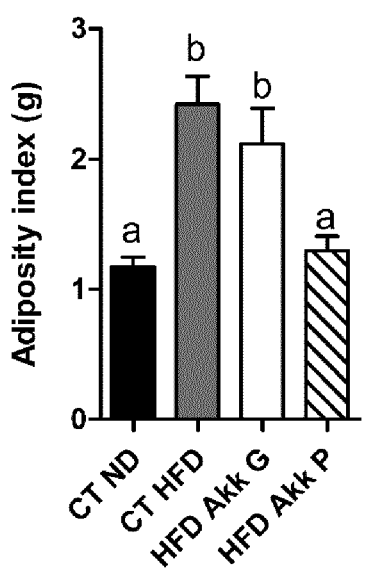
FIG. 6 is a histogram showing a reduction of adiposity index after administration of pasteurized *A. muciniphila* to a higher extent than live *A. muciniphila* grown on a non-mucus-based medium. Adiposity index (g), shown as the combined weight of the epididymal, subcutaneous and mesenteric adipose depots (n=16-19). Data are shown as mean±SEM. Data with different superscript letters are significantly different (P<0.05), according to one-way ANOVA analysis followed by Tukey post-hoc test.

In a second and third set of experiments, we treated high-fat diet mice with *A. muciniphila* grown on the non-mucus-based medium, either live or pasteurized, to confirm the effects obtained above. Mice fed standard chow were used as a control group, and treatment was carried on for five weeks. Treatment with *A. muciniphila* grown on non-mucus-based medium lead to a 10 to 15% decrease of body weight gain, fat mass gain and adiposity index in mice fed a high-fat diet, although without reaching statistical significance (FIGS. 5 and 6). Administration of pasteurized *A. muciniphila* completely normalized these parameters, once again showing a stronger effect following pasteurization.

Figure 7:
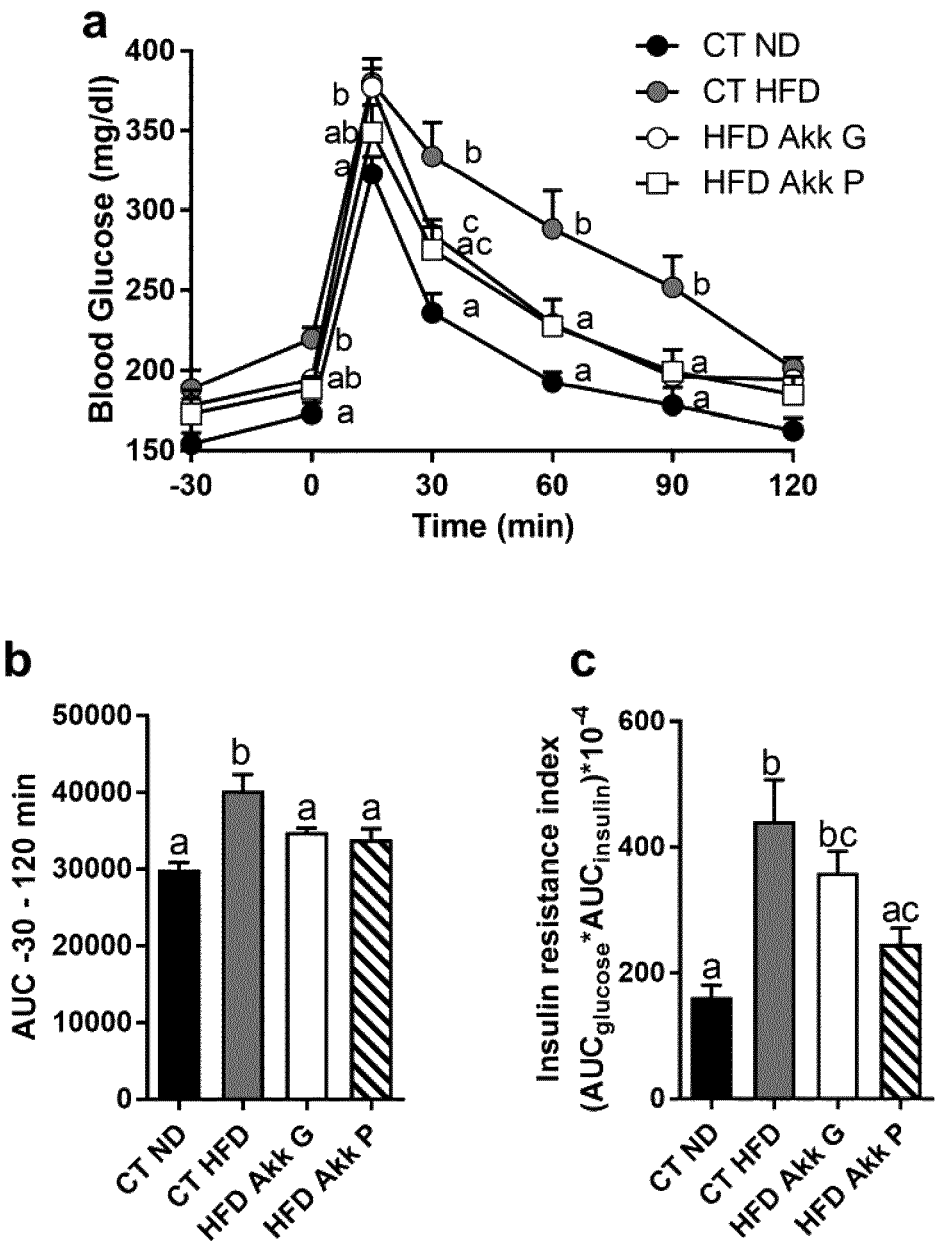
FIG. 7 is a set of histograms showing that administration of pasteurized *A. muciniphila* counteracts glucose intolerance in mice fed a high-fat diet to a higher extent than live *A. muciniphila*. Mice were fed a control diet (CT ND), a high-fat diet (CT HFD) and treated daily by oral gavage with sterile anaerobic PBS containing glycerol or *A. muciniphila* grown on a non-mucus-based medium, either live (HFD Akk G), or pasteurized (HFD Akk P) for 5 weeks. (a) Plasma glucose profile following 2 g/kg glucose oral challenge in freely moving mice (n=8-10). Data with different superscript letters are significantly different (P<0.05), according to two-way ANOVA analysis followed by Bonferonni post-test. (b) Mean area under the curve (AUC) measured between −30 and 120 min after glucose load (n=10). (c) Insulin resistance index, determined by multiplying the AUC of plasma glucose (−30 to 120 min) by the AUC of plasma insulin (−30 to 15 min) (n=8-10). Data are shown as mean±SEM. Data with different superscript letters are significantly different (P<0.05), according to one-way ANOVA analysis followed by Tukey post-hoc test.

We also obtained similar results in terms of glucose tolerance and insulin sensitivity. Indeed, while untreated mice fed a high-fat diet exhibited a higher AUC during the course of the OGTT (FIG. 7a-b), treatment with live or pasteurized *A. muciniphila* normalized this parameter. The IR index of mice treated with *A. muciniphila* grown on a non-mucus-based medium was 20% lower than for untreated high-fat diet-fed mice, but still significantly higher than for control mice. However, treatment with pasteurized *A. muciniphila* completely normalized the IR index with a two-fold decrease when compared to the untreated high-fat diet-fed group (FIG. 7c).

Figure 8:
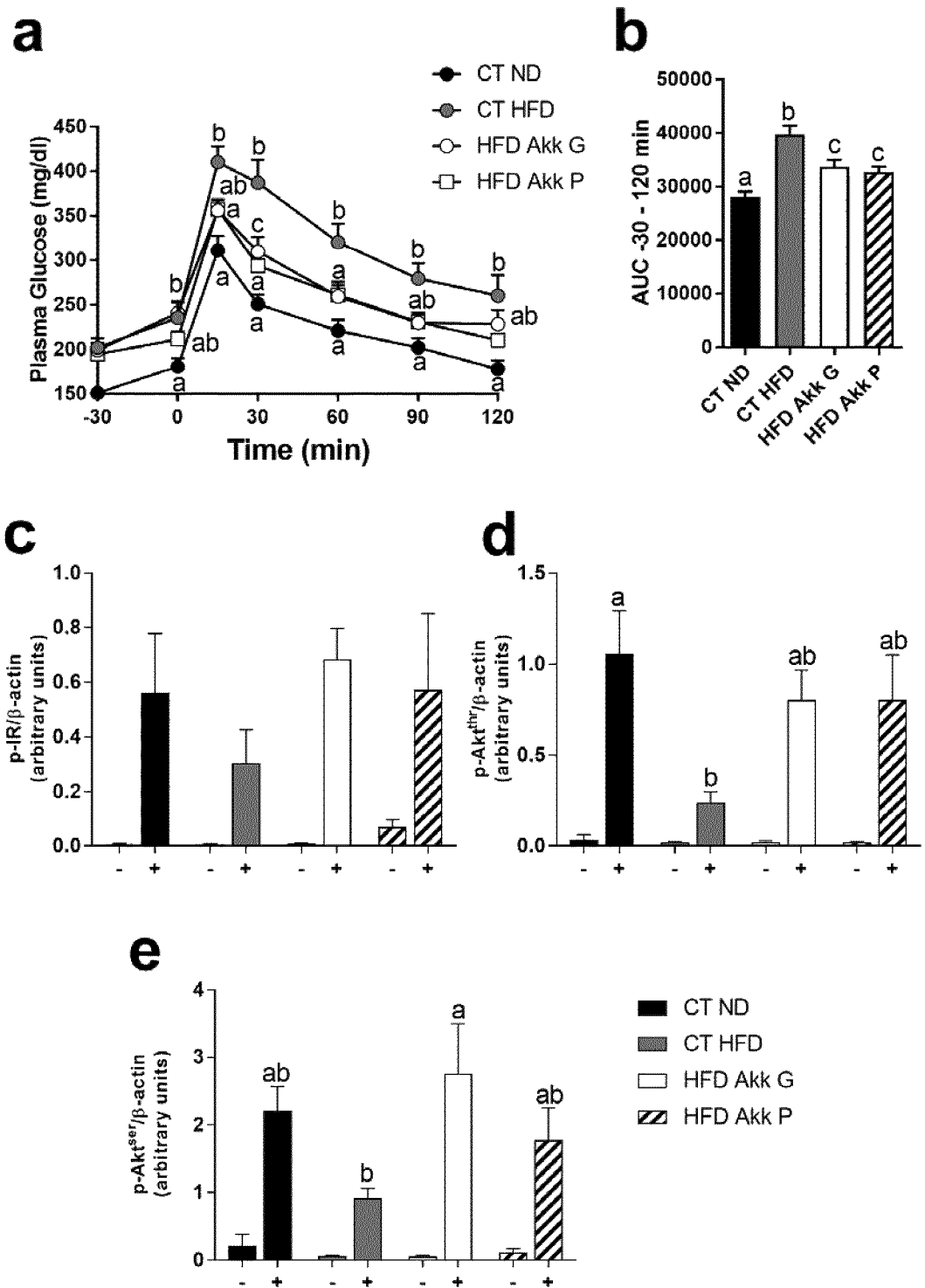
FIG. 8 is a set of graphs showing that administration of either live or pasteurized *A. muciniphila* counteracts glucose intolerance and insulin resistance in mice fed a high-fat diet. (a) Plasma glucose profile following 2 g/kg glucose oral challenge in freely moving mice (n=8-10). Data are shown as mean±SEM. Data with different superscript letters are significantly different (P<0.05), according to two-way ANOVA analysis followed by Bonferonni post-test. (b) Mean area under the curve (AUC) measured between −30 and 120 min after glucose load (n=8-10). Data are shown as mean±SEM. Data with different superscript letters are significantly different (P<0.05), according to one-way ANOVA analysis followed by Tukey post-hoc test. (c) Ratio of the control (−) and insulin-stimulated (+) p-IRβ on the loading control as measured by densitometry. (d) Ratio of the control and insulin-stimulated p-Akt$^{thr308}$ on the loading control as measured by densitometry. (e) Ratio of the control and insulin-stimulated p-Akt$^{ser473}$ on the loading control as measured by densitometry. (c-e) n=3-5. Data with different superscript letters are significantly different (P<0.05), according to two-way ANOVA analysis followed by Bonferonni post-test.

In the third set of experiments, while untreated mice fed a high-fat diet exhibited a higher AUC during the course of the OGTT, treatment with live or pasteurized *A. muciniphila* significantly decreased the AUC, showing an improvement of glucose tolerance (FIG. 8 a-b). In order to further investigate the effects of *A. muciniphila* on insulin sensitivity, in addition to the OGTT, we analyzed insulin-induced phosphorylation of the insulin receptor (IR) and its downstream mediator Akt in the liver at the threonine ($Akt^{thr}$) and serine ($Akt^{ser}$) sites after insulin or saline solution injection in the portal vein (FIG. 8 c-e). As previously described, untreated high-fat diet-fed mice displayed decreased phosphorylation of all assessed proteins when compared to CT ND mice, reaching significance for $Akt^{thr}$ (FIG. 8d). Treatment with *A. muciniphila* tended to counteract these effects, with significantly higher levels of p-$Akt^{ser}$ in mice treated with the live bacterium (FIG. 8e) when compared to untreated HFD-fed mice.

Figure 9:
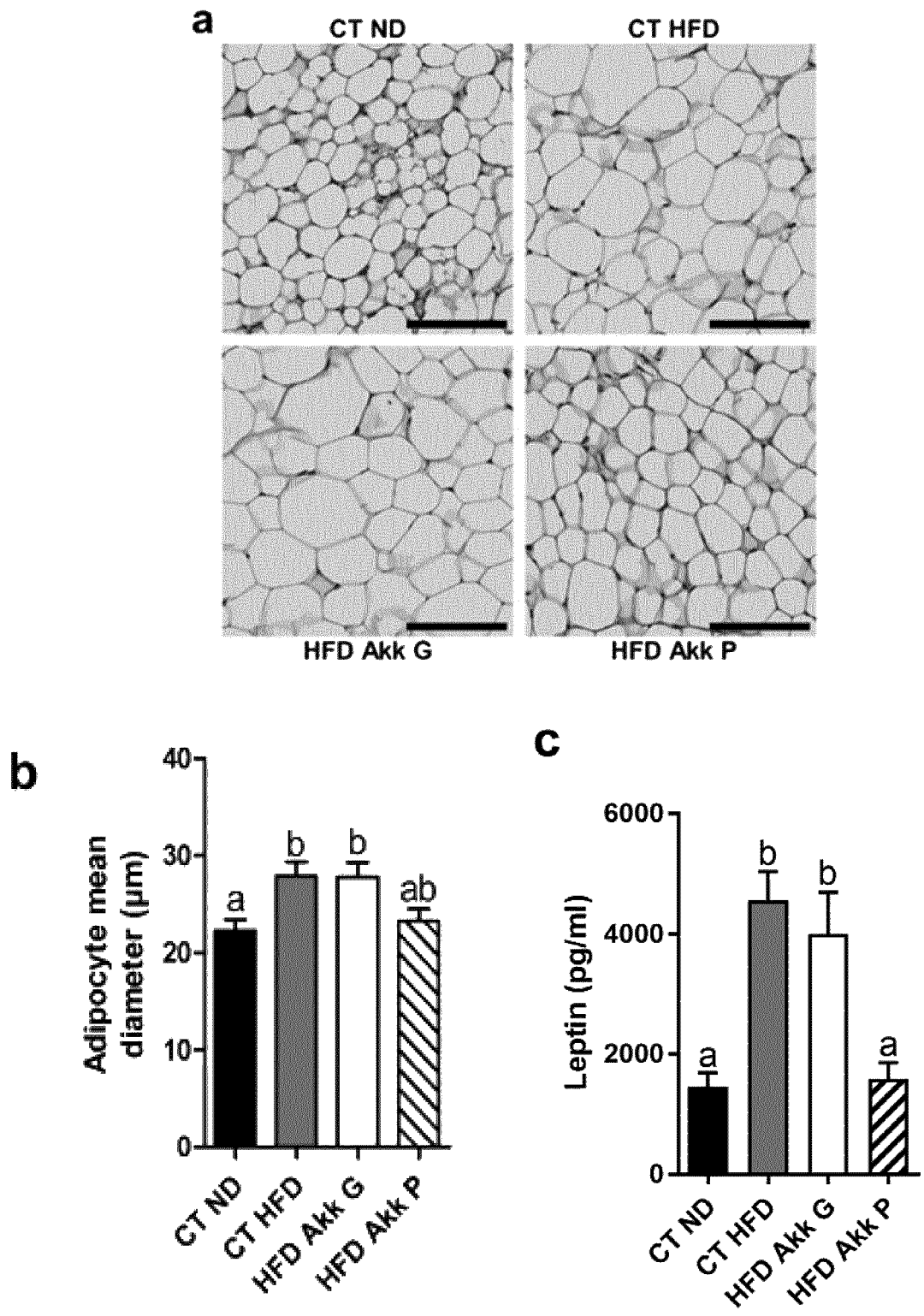
FIG. 9 is a photograph (a) and a histogram (b) showing that administration of pasteurized *A. muciniphila* counteracts the effects of a high-fat diet on the mean adipocyte diameter. Mice were fed a control diet (CT ND), a high-fat diet (CT HFD) and treated daily by oral gavage with sterile anaerobic PBS containing glycerol or *A. muciniphila* grown on a non-mucus-based medium, either live (HFD Akk G), or pasteurized (HFD Akk P) for 5 weeks. (a) Representative haematoxylin and eosin-stained picture of subcutaneous adipose tissue depots. Scale bar: 100 µm. (b) Mean adipocyte diameter (µm) determined by histological analysis (n=16-19). (c) Leptin plasma levels measured in the portal vein (pg/mL) (n=8-10). Data are shown as mean±SEM. Data with different superscript letters are significantly different (P<0.05), according to one-way ANOVA analysis followed by Tukey post-hoc test.

We then measured the mean adipocyte diameter in the subcutaneous adipose depot, as it is known to be increased in obesity and to contribute to the development of inflammation and insulin resistance (Rosen and Spiegelman, 2014. *Cell.* 156:20-44). In accordance with the literature, we observed that a high-fat diet leads to an increased diameter. Treatment with live *A. muciniphila* grown on a non-mucus-based did not affect the high-fat diet-induced-increased diameter. However, administration of pasteurized *A. muciniphila* restored the diameter to similar levels as in control mice (FIG. 9a-b). Treatment with pasteurized *A. muciniphila* also normalized leptin concentration to similar levels as observed in control mice (FIG. 9c).

Figure 10:
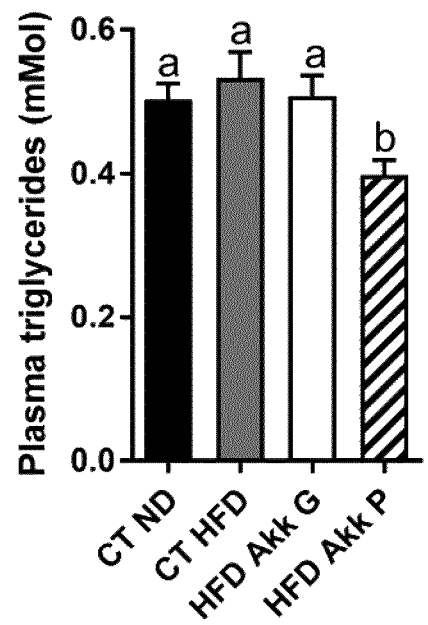
FIG. 10 is a histogram showing the reduction of plasma triglycerides levels after administration of pasteurized *A. muciniphila*. Mice were fed a control diet (CT ND), a high-fat diet (CT HFD) and treated daily by oral gavage with sterile anaerobic PBS containing glycerol or *A. muciniphila* grown on a non-mucus-based medium, either live (HFD Akk G), or pasteurized (HFD Akk P) for 5 weeks (n=16-19). Data are shown as mean±SEM. P value is indicated when two conditions were compared with an unpaired two-tailed Student's t-test (*: P<0.05).
Figure 11:
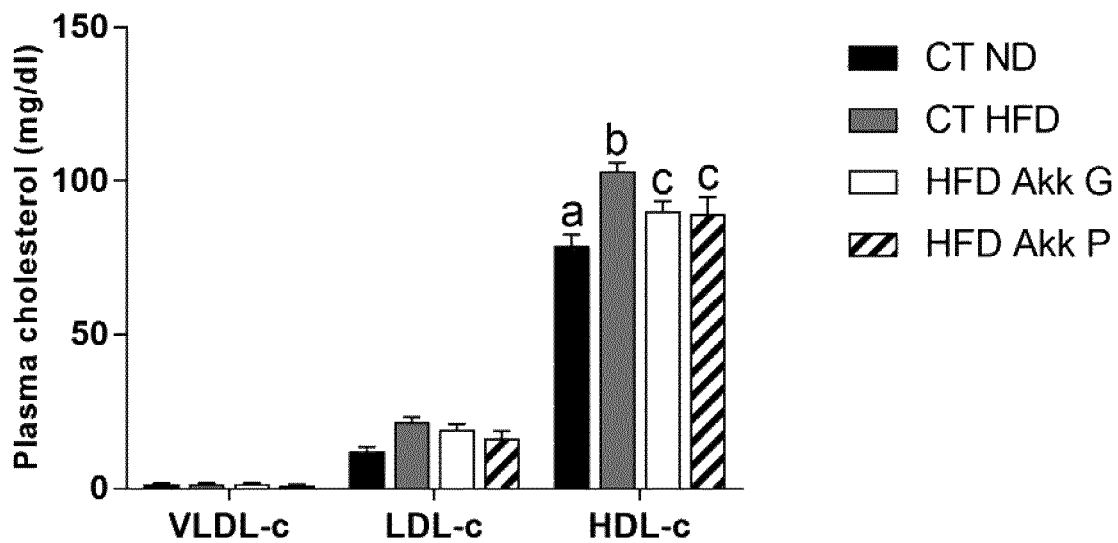
FIG. 11 is a histogram showing that the administration of either live or pasteurized *A. muciniphila* significantly decreases serum HDL-cholesterol and lead to a similar trend for LDL-cholesterol. Plasma VLDL, LDL and HDL cholesterol levels determined by fast protein liquid chromatography (FPLC). Mice were fed a control diet (CT ND), a high-fat diet (CT HFD) and treated daily by oral gavage with sterile anaerobic PBS containing glycerol or *A. muciniphila* grown on a non-mucus-based medium, either live (HFD Akk G), or pasteurized (HFD Akk P) for 5 weeks (n=8-10). Data with different superscript letters are significantly different (P<0.05), according to two-way ANOVA analysis followed by Bonferonni post-test.

The next parameter analyzed concerned the dyslipidemia induced by high-fat diet feeding. We assessed the effects of *A. muciniphila* on hypertriglyceridemia and hypercholesterolemia, which is associated with atherosclerosis and cardiovascular disease. Although no difference could be observed between control and untreated high-fat diet-fed mice, we observed that treatment with pasteurized *A. muciniphila* leads to a significant reduction (between 15 and 20%) of plasma triglyceride levels (FIG. 10). Regarding plasma cholesterol, treatment with either live or pasteurized *A. muciniphila* corrected the HFD-induced hypercholesterolemia, with significant decreases in plasma HDL-cholesterol and a similar trend for LDL-cholesterol (FIG. 11).

Figure 12:
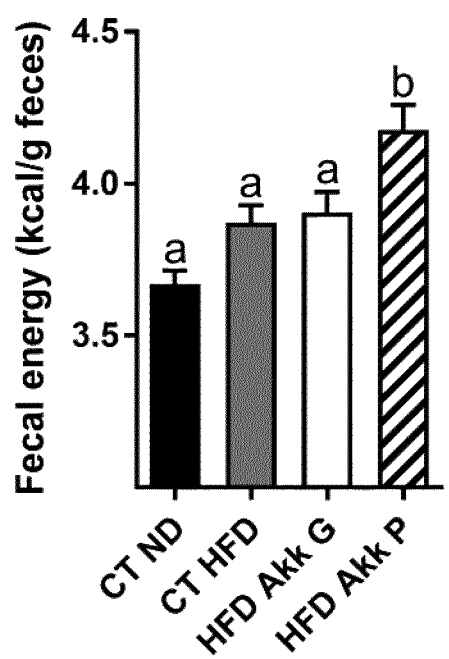
FIG. 12 is a histogram showing that the administration of pasteurized *A. muciniphila* increases energy excreted in the feces. Fecal energy measured by indirect bomb calorimetry (kcal/g feces) (n=5). Mice were fed a control diet (CT ND), a high-fat diet (CT HFD) and treated daily by oral gavage with sterile anaerobic PBS containing glycerol or *A. muciniphila* grown on a non-mucus-based medium, either live (HFD Akk G), or pasteurized (HFD Akk P) for 5 weeks. Data are shown as mean±SEM. Data with different superscript letters are significantly different (P<0.05), according to one-way ANOVA analysis followed by Tukey post-hoc test.

To further explain how live and pasteurized *A. muciniphila* reduce body weight and fat mass gain without affecting food intake on a high-fat diet, we measured fecal caloric content and found that it was significantly increased in mice treated with pasteurized *A. muciniphila* but not with live *A. muciniphila* (FIG. 12). These results suggested a decrease in energy absorption and therefore energy excretion in the feces following pasteurized *A. muciniphila* administration, which could, at least in part, explain the greater effects observed with pasteurized *A. muciniphila*.

Figure 13:
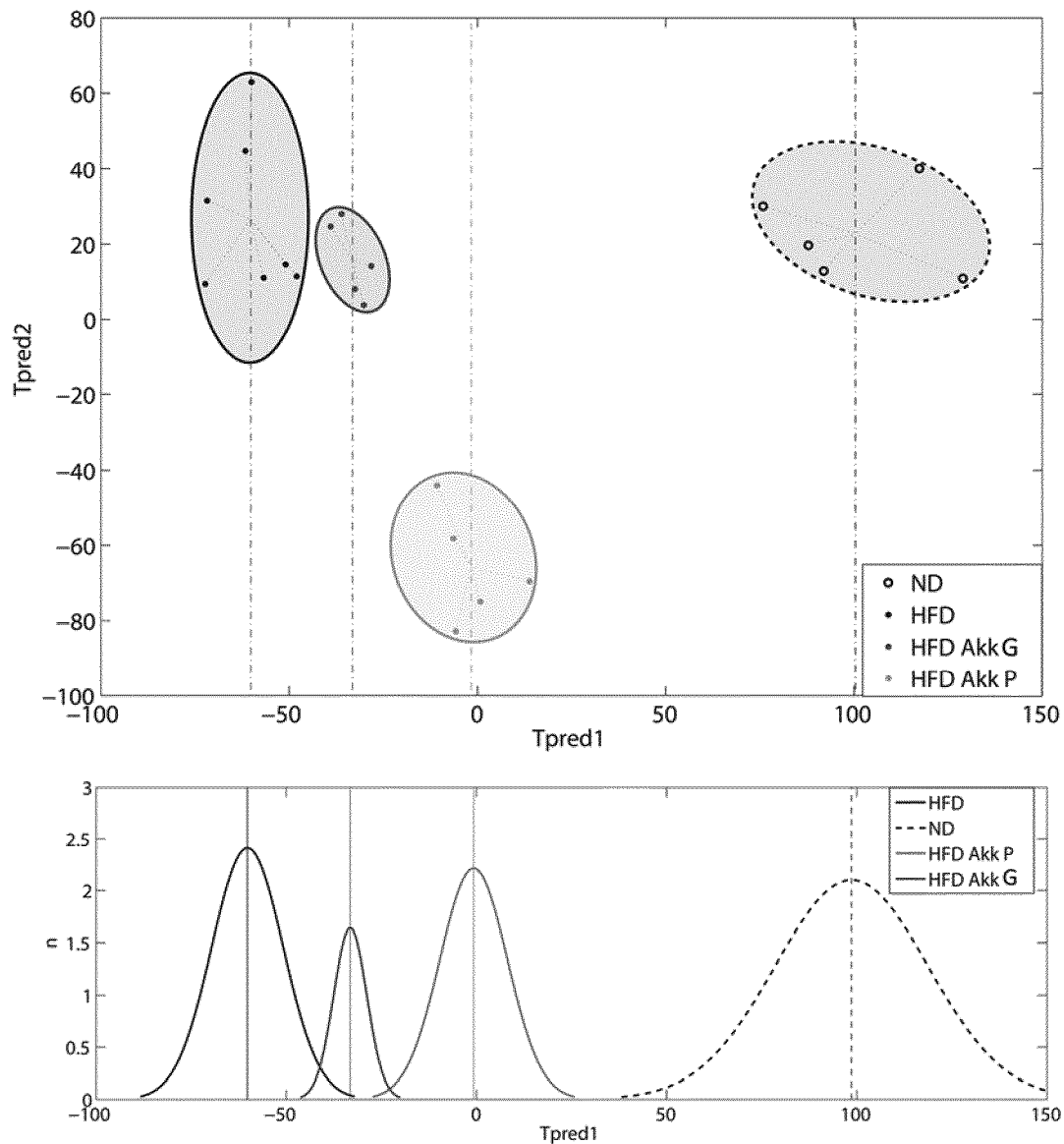
FIG. 13 is a graph showing that the administration of pasteurized *A. muciniphila* induces a larger correction of the HFD-induced shift in host urinary metabolomics profile than live *A. muciniphila*. (a) Orthogonal Partial Least Squares discriminant analysis (OPLS-DA) score plots for urine metabolic profiles (n=5-7). (b) Impact of all treatments on the predictive component 1 of the OPLS-DA analysis. Mice were fed a control diet (CT ND), a high-fat diet (CT HFD) and treated daily by oral gavage with sterile anaerobic PBS containing glycerol or *A. muciniphila* grown on a non-mucus-based medium, either live (HFD Akk G), or pasteurized (HFD Akk P) for 5 weeks.

We next assessed whether treatment with *A. muciniphila* could reduce the HFD-induced shift in the host urinary metabolome (FIG. 13). High-fat diet was the main factor influencing 1H NMR-based untargeted metabolic profiles on the first O-PLS-DA score (Tpred1) while treatment with pasteurized *A. muciniphila* clustered separately from all other groups regarding the second score (Tpred2, FIG. 13). This resulted in a normalization of the HFD-induced shift of 37% with the pasteurized bacterium, and 17% with the live bacterium (FIG. 13).

Altogether, these data suggest that the effects of *A. muciniphila* on host metabolism are mostly similar regardless of the growth medium used. More surprisingly, they also show that pasteurization potentiates the effects of *A. muciniphila*. This is of utmost interest as pasteurization could decrease biosafety issues associated with the use of a live bacterium while increasing the efficacy of *A. muciniphila* in the treatment of obesity and associated disorders.

Safety Assessment of Oral Administration of Live and Pasteurized *A. muciniphila* in Overweight or Obese Volunteers We evaluated the safety and tolerability of *A. muciniphila* oral administration in overweight and obese volunteers treated with different doses of live *A. muciniphila* (Akk S—$10^{10}$ and Akk S—10) or pasteurized *A. muciniphila* (Akk P—$10^{10}$) as part of an ongoing clinical study testing the efficacy of this bacterium against the metabolic syndrome. Anthropomorphic characteristics of the patients at the beginning of the intervention are reported in Table 3.

TABLE 3

Descriptive characteristics at the beginning of treatment for all subjects included in the clinical study (n = 5)

|  | Placebo | Akk S - $10^{10}$ | Akk S - $10^9$ | Akk P - $10^{10}$ |
|---|---|---|---|---|
| Sex (M/W) | 1/4 | 3/2 | 2/3 | 2/3 |
| Age (Years) | 53.00 ± 10.98 | 50.40 ± 4.72 | 50.60 ± 6.69 | 52.40 ± 7.99 |
| Body weight (Kg) | 102.60 ± 13.53 | 111.10 ± 19.52 | 103.80 ± 17.03 | 122.50 ± 12.67 |
| Body mass index (Kg/m$^2$) | 35.84 ± 5.98 | 38.48 ± 5.37 | 36.30 ± 3.12 | 40.71 ± 5.71 |
| Waist circumference (cm) | 116.60 ± 13.03 | 119.50 ± 12.35 | 115.60 ± 7.20 | 124.90 ± 8.10 |
| Fasting glycaemia (mg/dl) | 100.50 ± 10.52 | 96.13 ± 2.24 | 108.30 ± 12.91 | 106.30 ± 11.80 |

We analyzed several clinical parameters investigated in probiotics safety assessments (Jones et al., 2012. *Food. Chem. Toxicol.* 50:2216-2223; Burton et al., 2011. *Food Chem. Toxicol.* 49(9):2356-64; Wind et al., 2010. *Br. J. Nutr.* 104(12):1806-16) before and two weeks after starting the treatment. No significant changes on markers related to inflammation and hematology, kidney, liver and muscle function were observed with any formulation of *A. muciniphila* (FIG. 14A-K and Table 4).

TABLE 4

Descriptive characteristics at the beginning of treatment for all subjects included in the clinical study (n = 5)

|  | Placebo | | Akk S - $10^{10}$ | | Akk S - $10^9$ | | Akk P - $10^9$ | |
|---|---|---|---|---|---|---|---|---|
|  | Baseline | Safety | Baseline | Safety | Baseline | Safety | Baseline | Safety |
| Inflammation & Hematology | | | | | | | | |
| C-reactive protein (mg dl$^{-1}$) | 3.60 ± 1.67 | 4.40 ± 2.07 | 6.60 ± 5.18 | 6.40 ± 6.07 | 6.60 ± 5.18 | 6.40 ± 6.07 | 11.40 ± 14.33 | 15.20 ± 17.38 |
| White blood cells ($10^3$ µL$^{-1}$) | 6.43 ± 1.49 | 7.07 ± 1.68 | 7.91 ± 4.08 | 8.36 ± 4.17 | 7.91 ± 4.08 | 8.36 ± 4.17 | 6.89 ± 2.44 | 8.20 ± 1.61 |
| Prothrombin time (sec) | 11.38 ± 0.55 | 11.14 ± 0.44 | 10.92 ± 0.73 | 11.12 ± 0.80 | 10.92 ± 0.73 | 11.12 ± 0.80 | 11.28 ± 0.56 | 11.20 ± 0.56 |
| Liver enzymes | | | | | | | | |
| Alanine Aminostransferase activity (IU l$^{-1}$) | 24.00 ± 14.82 | 23.20 ± 15.71 | 27.40 ± 27.32 | 24.40 ± 13.85 | 27.40 ± 27.32 | 24.40 ± 13.85 | 29.20 ± 13.72 | 27.80 ± 12.05 |
| Aspartate | 17.00 ± | 16.60 ± | 19.33 ± | 17.67 ± | 19.33 ± | 17.67 ± | 23.00 ± | 19.80 ± |

TABLE 4-continued

Descriptive characteristics at the beginning of treatment for all subjects included in the clinical study (n = 5)

| | Placebo | | Akk S - $10^{10}$ | | Akk S - $10^9$ | | Akk P - $10^9$ | |
|---|---|---|---|---|---|---|---|---|
| | Baseline | Safety | Baseline | Safety | Baseline | Safety | Baseline | Safety |
| Aminotransferase activity (IU $l^{-1}$) | 6.33 | 6.35 | 9.48 | 5.05 | 9.48 | 5.05 | 9.14 | 7.98 |
| γ-Glutamyl-transferase activity (IU $l^{-1}$) | 22.40 ± 15.76 | 23.60 ± 18.05 | 40.40 ± 38.44 | 33.40 ± 24.42 | 40.40 ± 38.44 | 33.40 ± 24.42 | 45.20 ± 28.90 | 42.80 ± 24.94 |
| Kidney function | | | | | | | | |
| Urea (mg $dl^{-1}$) | 35.20 ± 10.26 | 30.00 ± 7.25 | 28.60 ± 9.42 | 30.40 ± 4.98 | 28.60 ± 9.42 | 30.40 ± 4.98 | 31.40 ± 2.88 | 43.40 ± 18.96 |
| Creatinine (mg $dl^{-1}$) | 0.73 ± 0.11 | 0.71 ± 0.10 | 0.78 ± 0.09 | 0.80 ± 0.15 | 0.78 ± 0.09 | 0.80 ± 0.15 | 0.83 ± 0.18 | 0.89 ± 0.21 |
| Glomerular filtration rate (mL $min^{-1}$ 1.73 $m^{-2}$) | 92.20 ± 22.52 | 95.20 ± 17.11 | 88.60 ± 10.06 | 88.60 ± 20.19 | 88.60 ± 10.06 | 88.60 ± 20.19 | 83.80 ± 14.17 | 78.00 ± 15.41 |
| Muscle enzymes | | | | | | | | |
| Creatinine Kinase activity (IU $l^{-1}$) | 78.80 ± 25.37 | 79.40 ± 28.06 | 92.40 ± 40.32 | 94.80 ± 38.11 | 92.40 ± 40.32 | 94.80 ± 38.11 | 162.40 ± 122.30 | 135.50 ± 87.53 |
| Lactate Dehydrogenase activity (IU $l^{-1}$) | 176.60 ± 19.86 | 167.20 ± 22.86 | 172.60 ± 20.74 | 176.20 ± 33.22 | 172.60 ± 20.74 | 176.20 ± 33.22 | 180.60 ± 17.70 | 171.40 ± 34.44 |

Moreover, the frequency of recorded adverse effects was similar in all groups (Table 5).

TABLE 5

Proportion of patients experiencing self-reported adverse effects (n = 5)

| | Placebo | Akk S - $10^{10}$ | Akk S - $10^9$ | Akk P - $10^9$ |
|---|---|---|---|---|
| Nausea | 1/5 | 0 | 2/5 | 1/5 |
| Flatulence | 0 | 1/5 | 3/5 | 1/5 |
| Bloating | 1/5 | 1/5 | 0 | 0 |
| Cramps | 1/5 | 1/5 | 0 | 1/5 |
| Borborygmi | 0 | 3/5 | 3/5 | 0 |
| Gastric reflux | 1/5 | 0 | 1/5 | 0 |

Borborygmi were reported by some patients treated with live *A. muciniphila*, but the difference with other groups was not significant.

While the number of subjects is limited, these first human data suggest that both live and pasteurized *A. muciniphila* are well tolerated in obese/overweight volunteers and appear safe for oral administration.

Furthermore, promising trends were observed in terms of fat mass, glycemia and inflammation markers at the end of the treatment period for patients treated with the high dose of live and/or pasteurized *A. muciniphila*.

The invention claimed is:

1. A method for treating a metabolic disorder in a human subject in need thereof comprising orally administering a therapeutically effective amount of pasteurized *Akkermansia muciniphila* or fragments thereof to the subject, wherein the *Akkermansia muciniphila* has been pasteurized at a temperature in a range of from 50° C. to 100° C. prior to administration, thereby treating the metabolic disorder in the subject.

2. The method according to claim 1, wherein said metabolic disorder is obesity.

3. The method according to claim 1, wherein said metabolic disorder is selected from the group consisting of metabolic syndrome; insulin-deficiency or insulin-resistance related disorders; Diabetes Mellitus including Type 2 Diabetes; glucose intolerance; abnormal lipid metabolism; atherosclerosis; hypertension; pre-eclampsia; cardiac pathology; stroke; non-alcoholic fatty liver disease; hyperglycemia; hepatic steatosis; liver diseases including fibrosis associated with obesity and abnormal liver functions, selected from changes in bile production and immunity; dyslipidemia; dysfunction of the immune system associated with overweight and obesity; inflammatory, immune and barrier function diseases selected from inflammatory bowel disease, Crohn's disease, ulcerative colitis, and irritable bowel syndrome; cardiovascular diseases; high cholesterol; elevated triglycerides; asthma; sleep apnea; osteoarthritis; neuro-degeneration; gallbladder disease; syndrome X; atherogenic dyslipidemia and cancer.

4. The method according to claim 1, wherein the therapeutically effective amount is an amount of *Akkermansia muciniphila* ranging from about $1.10^4$ to about $1.10^{12}$ cells.

5. The method according to claim 1, wherein the therapeutically effective amount of *Akkermansia muciniphila* is administered at least three times a week.

6. The method according to claim 1, wherein the therapeutically effective amount of *Akkermansia muciniphila* is co-administered with another probiotic strain and/or another bacteria and/or microorganisms with beneficial effects and/or with one or more prebiotics.

7. The method according to claim 1, wherein the therapeutically effective amount of *Akkermansia muciniphila* or fragment thereof is contained in a composition in association with an excipient.

8. The method according to claim 1, wherein the therapeutically effective amount of *Akkermansia muciniphila* or fragment thereof is contained in a nutritional composition.

9. The method according to claim 1, wherein the therapeutically effective amount of *Akkermansia muciniphila* or fragment thereof is contained in a pharmaceutical composition in association with a pharmaceutically acceptable vehicle.

10. A method for promoting weight loss in a human subject in need thereof comprising orally administering a therapeutically effective amount of pasteurized *Akkermansia muciniphila* or fragments thereof to the subject, wherein the *Akkermansia muciniphila* has been pasteurized at a temperature in a range of from 50° C. to 100° C. prior to administration, thereby promoting weight loss in the subject.

11. The method according to claim 10, wherein the method increases energy expenditure of the subject.

12. The method according to claim 10, wherein said method does not impact the food intake of said subject.

13. The method according to claim 10, wherein the therapeutically effective amount is an amount of *Akkermansia muciniphila* ranging from about $1.10^4$ to about $1.10^{12}$ cells.

14. The method according to claim 10, wherein the method increases satiety in the subject.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Primer RPL-19 Forward

<400> SEQUENCE: 1
gaaggtcaaa gggaatgtgt tca                                          23

<210> SEQ ID NO 2
<211> LENGTH: 21
<212> TYPE: DNA
<213> ORGANISM: Artificial Sequence
<220> FEATURE:
<223> OTHER INFORMATION: Primer RPL-19 Reverse

<400> SEQUENCE: 2
ccttgtctgc cttcagcttg t                                            21

-continued

```
<210> SEQ ID NO 3
<211> LENGTH: 19
<212> TYPE: DNA
<213> ORGANISM: Artificial Sequence
<220> FEATURE:
<223> OTHER INFORMATION: Primer Ocln Forward

<400> SEQUENCE: 3
atgtccggcc gatgctctc                                                   19

<210> SEQ ID NO 4
<211> LENGTH: 23
<212> TYPE: DNA
<213> ORGANISM: Artificial Sequence
<220> FEATURE:
<223> OTHER INFORMATION: Primer Ocln Reverse

<400> SEQUENCE: 4
tttggctgct cttgggtctg tat                                              23

<210> SEQ ID NO 5
<211> LENGTH: 22
<212> TYPE: DNA
<213> ORGANISM: Artificial Sequence
<220> FEATURE:
<223> OTHER INFORMATION: Primer Cldn3 Forward

<400> SEQUENCE: 5
tcatcggcag cagcatcatc ac                                               22

<210> SEQ ID NO 6
<211> LENGTH: 22
<212> TYPE: DNA
<213> ORGANISM: Artificial Sequence
<220> FEATURE:
<223> OTHER INFORMATION: Primer Cldn3 Reverse

<400> SEQUENCE: 6
acgatggtga tcttggcctt gg                                               22

<210> SEQ ID NO 7
<211> LENGTH: 27
<212> TYPE: DNA
<213> ORGANISM: Artificial Sequence
<220> FEATURE:
<223> OTHER INFORMATION: Primer Lyz1 Forward

<400> SEQUENCE: 7
gccaaggtct acaatcgttg tgagttg                                          27

<210> SEQ ID NO 8
<211> LENGTH: 23
<212> TYPE: DNA
<213> ORGANISM: Artificial Sequence
<220> FEATURE:
<223> OTHER INFORMATION: Primer Lyz1 Reverse

<400> SEQUENCE: 8
cagtcagcca gcttgacacc acg                                              23
```